United States Patent
Ju et al.

(10) Patent No.: US 10,449,270 B2
(45) Date of Patent: *Oct. 22, 2019

(54) COLLAGEN SCAFFOLDS, MEDICAL IMPLANTS WITH SAME AND METHODS OF USE

(71) Applicants: Young Min Ju, Winston-Salem, NC (US); Francis Moussy, Uxbridge (GB); Thomas J. Koob, Santa Fe, NM (US)

(72) Inventors: Young Min Ju, Winston-Salem, NC (US); Francis Moussy, Uxbridge (GB); Thomas J. Koob, Santa Fe, NM (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,003

(22) Filed: Feb. 27, 2017

(65) Prior Publication Data

US 2017/0173216 A1 Jun. 22, 2017

Related U.S. Application Data

(60) Division of application No. 14/642,137, filed on Mar. 9, 2015, now Pat. No. 9,579,422, which is a division of application No. 13/869,460, filed on Apr. 24, 2013, now Pat. No. 8,975,372, which is a continuation of application No. 11/821,320, filed on Jun. 22, 2007, now abandoned.

(60) Provisional application No. 60/805,495, filed on Jun. 22, 2006.

(51) Int. Cl.
| | |
|---|---|
| *A61L 27/24* | (2006.01) |
| *C07K 14/78* | (2006.01) |
| *A61L 27/48* | (2006.01) |
| *A61L 27/34* | (2006.01) |
| *A61L 31/04* | (2006.01) |
| *A61L 31/10* | (2006.01) |
| *A61L 27/54* | (2006.01) |
| *A61L 31/12* | (2006.01) |
| *A61B 5/145* | (2006.01) |
| *A61B 5/1486* | (2006.01) |
| *A61L 27/18* | (2006.01) |
| *A61L 27/56* | (2006.01) |

(52) U.S. Cl.
CPC .......... *A61L 27/48* (2013.01); *A61B 5/14542* (2013.01); *A61B 5/14865* (2013.01); *A61L 27/18* (2013.01); *A61L 27/24* (2013.01); *A61L 27/34* (2013.01); *A61L 27/54* (2013.01); *A61L 27/56* (2013.01); *A61L 31/044* (2013.01); *A61L 31/10* (2013.01); *A61L 31/129* (2013.01); *A61B 5/1486* (2013.01); *A61L 2400/02* (2013.01); *A61L 2400/18* (2013.01); *A61L 2420/02* (2013.01)

(58) Field of Classification Search
CPC ..... A61L 27/24; D06M 2101/14; C07K 14/78
See application file for complete search history.

(56) References Cited

U.S. PATENT DOCUMENTS

| | | |
|---|---|---|
| 4,693,715 A | 9/1987 | Abel, Jr. |
| 5,108,428 A | 4/1992 | Capecchi et al. |
| 5,114,627 A | 5/1992 | Civerchia |
| 5,304,595 A | 4/1994 | Rhee et al. |
| 5,306,500 A | 4/1994 | Rhee et al. |
| 5,308,889 A | 5/1994 | Rhee et al. |
| 5,420,248 A | 5/1995 | Devictor et al. |
| 5,507,804 A | 4/1996 | Llanos |
| 5,523,348 A | 6/1996 | Rhee et al. |
| 5,836,313 A | 11/1998 | Perez et al. |
| 6,106,552 A | 8/2000 | Lacombe et al. |
| 6,277,394 B1 | 8/2001 | Sierra |
| 6,277,397 B1 | 8/2001 | Shimizu |
| 6,335,007 B1 | 1/2002 | Shimizu |
| 6,387,663 B1 | 5/2002 | Hall et al. |
| 6,565,960 B2 | 5/2003 | Koob et al. |
| 6,689,153 B1 | 2/2004 | Skiba |
| 6,713,537 B1 | 3/2004 | Ueda et al. |

(Continued)

FOREIGN PATENT DOCUMENTS

| | | |
|---|---|---|
| EP | 0177573 B1 | 1/1992 |
| JP | 5-506172 | 9/1993 |

(Continued)

OTHER PUBLICATIONS

Ahmed, S. et al. "Tissue Implanted Glucose Needle Electrodes: Early Sensor Stabilisation and Achievement of Tissue-Blood Correlation During the Run in Period" *Analytica Chimica Acta*, 2005, pp. 153-161, vol. 537.

(Continued)

*Primary Examiner* — Karen Cochrane Carlson

(74) *Attorney, Agent, or Firm* — Saliwanchik, Lloyd & Eisenschenk

(57) ABSTRACT

The subject invention concerns non-degradable three dimensional porous collagen scaffolds and coatings. These scaffolds can be prepared around sensors for implantation into a body. A specific embodiment of the invention concerns implantable glucose sensors. Sensors comprising a collagen scaffold of the invention have improved biocompatibility by minimizing tissue reactions while stimulating angiogenesis. The subject invention also concerns methods for preparing collagen scaffolds of the invention. The subject invention also concerns sensors that have a collagen scaffold of the invention around the exterior of the sensor.

10 Claims, 32 Drawing Sheets

(56) References Cited

U.S. PATENT DOCUMENTS

| | | |
|---|---|---|
| 6,821,530 B2 | 11/2004 | Koob et al. |
| 6,887,933 B2 | 5/2005 | Even |
| 6,974,679 B2 | 12/2005 | Andre et al. |
| 6,976,997 B2 | 12/2005 | Noolandi et al. |
| 7,084,082 B1 | 8/2006 | Shimizu |
| 7,162,289 B2 | 1/2007 | Shah et al. |
| 2002/0123805 A1 | 9/2002 | Murray et al. |
| 2003/0204023 A1 | 10/2003 | Koob et al. |
| 2005/0020506 A1 | 1/2005 | Drapeau et al. |
| 2006/0008500 A1 | 1/2006 | Chavan et al. |
| 2006/0100138 A1 | 5/2006 | Olsen et al. |
| 2006/0129234 A1 | 6/2006 | Phaneuf et al. |
| 2006/0257377 A1 | 11/2006 | Atala et al. |
| 2007/0190160 A1 | 8/2007 | Turos et al. |

FOREIGN PATENT DOCUMENTS

| | | |
|---|---|---|
| WO | WO 91/15993 | 10/1991 |
| WO | WO 2004/101017 A2 | 11/2004 |
| WO | WO 2005/020933 A2 | 3/2005 |
| WO | WO0115259 A2 * | 12/2005 |

OTHER PUBLICATIONS

Norton, L.W. et al. "In Vitro Characterization of Vascular Endothelial Growth Factor and Dexamethasone Releasing Hydrogels for Implantable Probe Coatings" *Biomaterials*, 2005, pp. 3285-3297, vol. 26.

Quinn, C.A.P. et al. "Biocompatible, Glucose-Permeable Hydrogel for in Situ Coating of Implantable Biosensors" *Biomaterials*, 1997, pp. 1665-1670, vol. 18.

Yu, B. et al. "A Long-Term Flexible Minimally-Invasive Implantable Glucose Biosensor Based on an Epoxy-Enhanced Polyurethane Membrane" *Biosensors and Bioelectronics*, 2006, pp. 2275-2282, vol. 21.

Zong, S. et al. "Hydrogen Peroxide Biosensor Based on Hemoglobin Modified Zirconia Nanoparticles-Grafted Collagen Matrix" *Analytica Chimica Acta*, 2007, pp. 361-366, vol. 582.

Koob, T. et al. "Material Properties of Polymerized NDGA-collagen composite fibers: development of biologically based tendon constructs" *Biomaterials*, 2002, pp. 203-212, vol. 23.

Koob, T. et al. "Mechanical and thermal properties of novel polymerized NDGA-gelatin hydrogels" *Biomaterials*, 2003, pp. 1285-1292, vol. 24.

Angele et al. "Influence of different collagen species on physicochemical properties of crosslinked collagen matrices" *Biomaterials*, 2004, pp. 2831-2841, vol. 25, No. 14.

Armour et al. "Application of chronic intravascular blood glucose sensor in dogs" *Diabetes*, 1990, pp. 1519-1526, vol. 39, No. 12, abstract.

Ash et al. "Subcutaneous capillary filtrate collector for measurement of blood glucose" *Asaio J*, 1992, pp. M416-M420, vol. 38, No. 3, abstract.

Barbani et al. "Bioartificial materials based on collagen: 1. Collagen cross-linking with gaseous glutaraldehyde" *J Biomater Sci Polym Ed*, 1995, pp. 461-469, vol. 7, No. 6, abstract.

Bindra et al. "Reach G. Design and in vitro studies of a needle-type glucose sensor for subcutaneous monitoring" *Anal Chem*, 1991, pp. 1692-1696, vol. 63, No. 17, abstract.

Ertefai et al. "Physiological preparation for studying the response of subcutaneously implanted glucose and oxygen sensors" *J Biomed Eng*, 1989, pp. 362-368, vol. 11, No. 5, abstract.

Frost et al. "Implantable chemical sensors for real-time clinical monitoring: progress and challenges" *Curr Opin Chem Biol*, 2002, pp. 633-641, vol. 6, No. 5.

Huang-Lee et al. "Biochemical changes and cytotoxicity associated with the degradation of polymeric glutaraldehyde derived crosslinks" *J Biomed Mater Res*, 1990, pp. 1185-1201, vol. 24, No. 9.

Johnson et al. "In vivo evaluation of an electroenzymatic glucose sensor implanted in subcutaneous tissue" *Biosens Bioelectron*, 1992, pp. 709-714, vol. 7, No. 10.

Joseph et al. "Glucose Sensors" In: Wnek GE, Bowlin GL, editors. Encyclopedia of biomaterials and biomedical engineering. New York: Marcel Dekker, 2004, pp. 683-692, abstract.

Kerner et al. "The function of a hydrogen peroxide-detecting electroenzymatic glucose electrode is markedly impaired in human sub-cutaneous tissue and plasma" *Biosens Bioelectron*, 1993, pp. 473-482, vol. 8, Nos. 9-10.

Khor E. "Methods for the treatment of collagenous tissues for bioprostheses" *Biomaterials*, 1997, pp. 95-105, vol. 18, No. 2.

Koob et al. "Biocompatibility of NDGA-polymerized collagen fibers. I. Evaluation of cytotoxicity with tendon fibroblasts in vitro" *J Biomed Mater Res*, 2001, pp. 31-39, vol. 56, No. 1.

Koob et al. "Biocompatibility of NDGA-polymerized collagen fibers. II. Attachment, proliferation, and migration of tendon fibroblasts in vitro" *J Biomed Mater Res*, 2001, pp. 40-48, vol. 56, No. 1.

Koob T.J. "Biomimetic approaches to tendon repair" *Comp Biochem Physiol A Mol Integr Physiol*, 2002, pp. 1171-1192, vol. 133, No. 4.

Koudelka et al. "In-vivo behaviour of hypodermically implanted microfabricated glucose sensors" *Biosens Bioelectron*, 1991, pp. 31-36, vol. 6, No. 1.

Lee et al. "Biomedical applications of collagen" *Int J Pharm*, 2001, pp. 1-22, vol. 221, Nos. 1-2.

Lee et al. "Glucose measurements with sensors and ultrasound" *Ultrasound Med Biol*, 2005, pp. 971-977, vol. 31, No. 7.

Long et al. "Strategies for testing long-term transcutaneous amperometric glucose sensors" *Diabetes Technol Ther*, 2005, pp. 927-936, vol. 7, No. 6.

Meyerhoff et al. "On line continuous monitoring of subcutaneous tissue glucose in men by combining portable glucosensor with microdialysis" *Diabetologia*, 1992, pp. 1087-1092, vol. 35, No. 11.

Moscone et al. "Microdialysis and glucose biosensor for in vivo monitoring" *Ann Biol Clin (Paris)*, 1992, pp. 323-327, vol. 50, No. 5, abstract.

Moussy et al. "Performance of subcutaneously implanted needle-type glucose sensors employing a novel trilayer coating" *Anal Chem*, 1993, pp. 2072-2077, vol. 65, No. 15.

Moussy et al. "A miniaturized Nafion-based glucose sensor: in vitro and in vivo evaluation in dogs" *Int J Artif Organs*, 1994, pp. 88-94, vol. 17, No. 2, abstract.

Moussy et al. "Prevention of the rapid degradation of subcutaneously implanted Ag/AgCl reference electrodes using polymer coatings" *Anal Chem*, 1994, pp. 674-679, vol. 66, No. 5.

Moussy et al. "In vitro and in vivo performance and lifetime of perfluorinated ionomer-coated glucose sensors after high-temperature curing" *Anal Chem*, 1994, pp. 3882-3888, vol. 66, No. 22.

Pachence J.M. "Collagen-based devices for soft tissue repair" *J Biomed Mater Res*, 1996, pp. 35-40, vol. 33, No. 1.

Patel et al. "Preparation and characterization of freeze-dried chitosan-poly(ethylene oxide) hydrogels for site-specific antibiotic delivery in the stomach" *Pharm Res*, 1996, pp. 588-593, vol. 13, No. 4, abstract.

Pickup et al. "In vivo molecular sensing in diabetes mellitus: an implantable glucose sensor with direct electron transfer" *Diabetologia*, 1989, pp. 213-217, vol. 32, No. 3.

Pieper et al. "Crosslinked type II collagen matrices: preparation, characterization, and potential for cartilage engineering" *Biomaterials*, 2002, pp. 3183-3192, vol. 23, No. 15.

Quinn et al. "Photo-crosslinked copolymers of 2-hydroxyethyl methacrylate, poly(ethylene glycol) tetra-acrylate and ethylene dimethacrylate for improving biocompatibility of biosensors" *Biomaterials*, 1995, pp. 389-396, vol. 16, No. 5.

Reddy et al. "Ion exchanger modified PVC membranes—selectivity studies and response amplification of oxalate and lactate enzyme electrodes" *Biosens Bioelectron*, 1997, pp. 1003-1012, vol. 12, Nos. 9-10.

Rigby et al. "Open flow microperfusion: approach to in vivo glucose monitoring" *Med Biol Eng Comput*, 1995, pp. 231-234, vol. 33, No. 2, abstract.

Sharkawy et al. "Engineering the tissue which encapsulates subcutaneous implants. I. Diffusion properties" *J Biomed Mater Res*, 1997, pp. 401-412, vol. 37, No. 3.

(56) References Cited

OTHER PUBLICATIONS

Shaw et al. "In vitro testing of a simply constructed, highly stable glucose sensor suitable for implantation in diabetic patients" *Biosens Bioelectron*, 1991, pp. 401-406, vol. 6, No. 5.

Sheu et al. "Characterization of collagen gel solutions and collagen matrices for cell culture" *Biomaterials*, 2001, pp. 1713-1719, vol. 22, No. 13.

Shichiri, et al. "In vivo characteristics of needle-type glucose sensor—measurements of subcutaneous glucose concentrations in human volunteers" *Horm Metab Res Suppl*, 1988, pp. 17-20, vol. 20, abstract.

Sung et al. "Cross-linking characteristics of biological tissues fixed with monofunctional or multifunctional epoxy compounds" *Biomaterials* 1996, pp. 1405-1410, vol. 17, No. 14.

Van Luyn et al. "Secondary cytotoxicity of cross-linked dermal sheep collagens during repeated exposure to human fibroblasts" *Biomaterials*, 1992, pp. 1017-1024, vol. 13, No. 14, abstract.

Wilkins et al. "Integrated implantable device for long-term glucose monitoring" *Biosens Bioelectron*, 1995, pp. 485-494, vol. 10, No. 5.

Yu et al. "A long-term flexible minimally-invasive implantable glucose biosensor based on an epoxy-enhanced polyurethane membrane" *Biosens Bioelectron*, 2006, pp. 2275-2282, vol. 21, No. 12.

Amalvy, J.I. "Semicontinuous emulsion polymerization of methyl methacrylate, ethyl acrylate, and methacrylic acid" *Journal of Applied Polymer Science*, 1996, pp. 339-344, vol. 59.

Capek, I. et al. "Emulsion copolymerization of methyl methacrylate with ethyl acrylate, 1: Effect of the initiator concentration on the polymerization behaviour" *Makromol. Chem.*, 1986, pp. 2063-2072, vol. 187.

Chen, G. et al. "A hybrid network of synthetic polymer mesh and collagen sponge" *Chem. Commun.*, 2000, pp. 1505-1506.

Chen, G. et al. "Culturing of skin fibroblasts in a thin PLGA-collagen hybrid mesh" *Biomaterials*, 2005, pp. 2559-2566, vol. 26.

Coombes, A.G.A. et al. "Biocomposites of non-crosslinked natural and synthetic polymers" *Biomaterials*, 2002, pp. 2113-2118, vol. 23.

Koob, T.J. "Collagen Fixation" *Encyclopedia of biomaterials and biomedical engineering*, Wnek G.E., Bowlin G.L., editors, 2004, pp. 335-347, Marcel Dekker, New York.

Rao, K.P. et al. "Collagen-poly(methyl methacrylate) graft copolymers: Effect of aqueous organic solvent system and salts on copolymer composition" *Die Makromolekulare Chemie*, 1974, pp. 729-737, vol. 175.

Venugopal, J. et al. "Fabrication of modified and functionalized polycaprolactone nanofibre scaffolds for vascular tissue engineering" *Nanotechnology*, 2005, pp. 2138-2142, vol. 16.

Yang, S. et al. "The design of scaffolds for use in tissue engineering. Part I. Traditional factors" *Tissue Engineering*, 2001, pp. 679-689, vol. 7, No. 6.

Chen, G. et al. "Preparation of biodegradable hybrid sponge and its application to three-dimensional chondrocyte cultures" *The Japanese Journal of Artificial Organs*, 2000, vol. 29, No. 2, pp. 463-467.

Chen, G. et al. "Fabrication of biodegradable hybrid sponge" *The Japan Society of Mechanical Engineers*, 1999, vol. 11, pp. 380-381.

Chen, G. et al. "Biodegradable hybrid scaffolds for tissue engineering" *Proceeding of Intelligent Material Symposium*, 2001, vol. 10, pp. 70-71.

Kanematsu, A. et al. "Collagenous matrices as release carriers of exogenous growth factors" *Biomaterials*, 2004, vol. 25, No. 18, pp. 4513-4520.

Ward, W.K. et al. "The effect of local subcutaneous delivery of vascular endothelial growth factor on the function of a chronically implanted amperometric glucose sensor" *Diabetes Technology & Therapeutics*, 2004, vol. 6, No. 2, pp. 137-145.

Updike, S. et al. "A subcutaneous glucose sensor with improved, longevity, dynamic range, and stability of calibration" *Diabetes Care*, 2000, vol. 23, No. 2, pp. 208-214.

Cell Biology/Introduction/Cell Size (Wikibooks, collection of open-content textbooks, online reference, accessed on Jul. 21, 2010).

Dagalakis, N. et al. "Design of an artificial skin. Part III. Control of pore structure" *J. Biomed. Mat. Res.*, 1980, 14:511-528.

\* cited by examiner

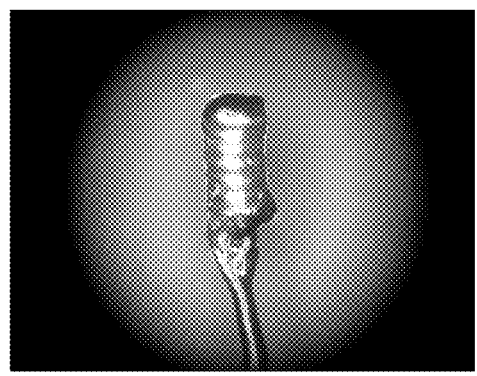 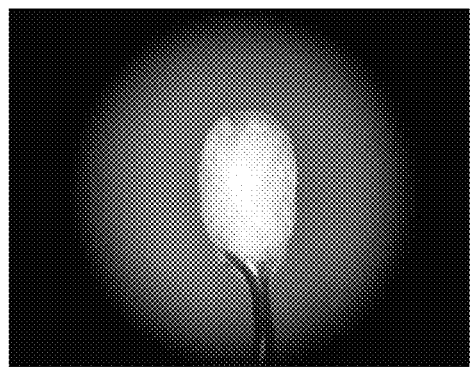
FIG. 8A    FIG. 8B
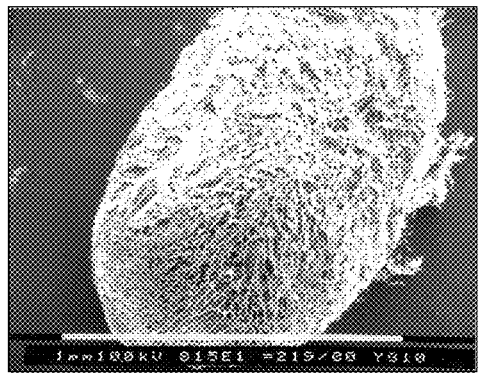 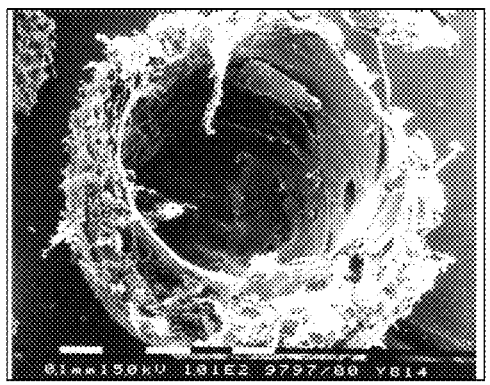
FIG. 8C    FIG. 8D

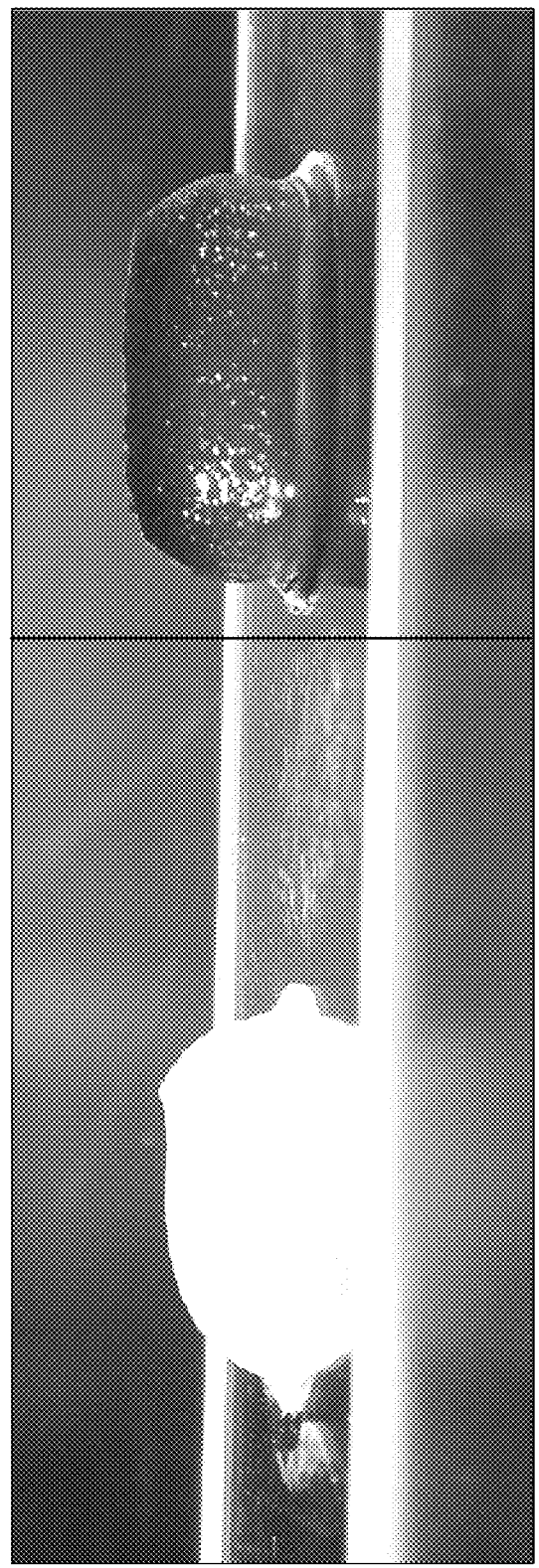

COLLAGEN SCAFFOLDS, MEDICAL IMPLANTS WITH SAME AND METHODS OF USE

CROSS-REFERENCE TO RELATED APPLICATIONS

The present application is a divisional of U.S. application Ser. No. 14/642,137, filed Mar. 9, 2015, which is a divisional of U.S. application Ser. No. 13/869,460, filed Apr. 24, 2013, now U.S. Pat. No. 8,975,372, which is a continuation of U.S. application Ser. No. 11/821,320, filed Jun. 22, 2007, now abandoned, which claims the benefit of U.S. Provisional Application Ser. No. 60/805,495, filed Jun. 22, 2006, each of which is hereby incorporated by reference herein in its entirety, including any figures, tables, nucleic acid sequences, amino acid sequences, and drawings.

GOVERNMENT SUPPORT

This invention was made with government support under R01 EB001640 awarded by National Institutes of Health. The government has certain rights in the invention.

FIELD OF THE INVENTION

This invention relates to implantable biosensors and medical devices. More specifically, this invention relates to collagen scaffold coverings for implantable sensors and/or other medical devices promoting biocompatibility.

BACKGROUND OF THE INVENTION

Chronically implantable devices may provoke inflammation and/or fibrosis from tissue trauma or tissue response to the foreign body. See, e.g., Reichert et al., Handbook of Biomaterial Evaluation, Ch. 28 Biosensors, pp. 439-460, (Von Recum A., editor) (1999); Wisniewski et al., J Anal Chem 2000; 366 (6-7) (p. 611-621).

Implanted devices may also cause other unwanted bioreactions. For example, recently, researchers have stated that drug-coated stents might cause adverse reactions leading to blood clot formation in some patients. See Lagerqvist et al., *Long-Term Outcomes with Drug-Eluting Stents versus Bare-Metal Stents in Sweden*, New England Jnl. Of Medicine, Mar. 8, 2007.

Other chronically implantable devices that may invoke unwanted bioreactions are biosensors. For example, in order to maintain near normal blood glucose levels (70-120 mg/dL), diabetic patients widely use over-the-counter glucose meters, which require finger pricking to obtain blood samples several times a day. The pain (Lee et al., 2005), inconvenience, and discomfort of self-monitoring of blood glucose (SMBG) are frequently obstacles to effective patient compliance and optimal management of diabetes. During the past 20 years many kinds of continuous glucose monitoring systems have been studied including sensors implanted in the subcutaneous tissue (Moussy et al., 1993; Johnson et al., 1992; Koudelka et al., 1991; Bindra et al., 1991; Pickup et al., 1989; Shichiri et al., 1986; and Ertefai et al., 1989), sensors implanted in the vascular bed (Armour et al., 1990; Frost et al., 2002), and determining glucose concentration in interstitial fluid sampled using a micro dialysis device (Ash et al., 1992; Meyerhoff et al., 1992; Moscone et al., 1992). Although several studies of implantable glucose sensors have been reported, it is believed that none of these biosensors are reliably capable of continuously monitoring glucose levels during long-term implantation. Progressive loss of sensor function occurs due in part to biofouling and to the consequences of a foreign body response such as inflammation, fibrosis, and loss of vasculature (Reichert et al., 1992; Reichert et al., 1999; Sharkawy et al., 2007). Some researchers have modified the surface of the sensors to reduce membrane biofouling in vivo. In an approach to reduce protein adsorption, Quinn et al., 1995 used poly(ethylene glycol) (PEG) in a polyhydroxyethylmethacrylate (PHEMA) matrix. Since the PEG chains tend to stand up perpendicular to the membrane surface, they provide a water-rich phase that resists binding of many protein molecules. Rigby et al., 1995 and Reddy et al., 1997 reduced protein adsorption by using diamond-like carbon, so-called "inert" materials. Shichiri et al., 1988 incorporated an alginate/polylysine gel layer at the sensor. Shaw et al., 1991 reported improvement in biocompatibility of a biosensor coated with PHEMA/PU (polyurethane). Wilkins et al., 1995 and Moussy et al. introduced NAFION (perfluorosulphonic acid) membrane (Du Pont), to reduce "biofouling" on the surface of the sensor and reduce interference from urate and ascorbate (Moussy et al., 1993; Moussy et al., 1994a; Moussy et al., 1994b; Moussy et al., 1994c). Armour et al., 1990 coated their sensor tips with cross-linked albumin and Kerner et al., 1993 developed cellulose-coated sensors to improve sensor blood compatibility. However, it is believed that none of these approaches has been satisfactory for long term, stable glucose monitoring.

Collagen and its derived matrices are used extensively as natural polymers in the biomedical field including tissue engineering due to its low antigenicity, its biodegradability and its good mechanical, haemostatic and cell-binding properties (Sheu et al., 2001; Pieper et al., 2002; Chvapil et al., 1973; Pachence et al., 1996; and Lee et al., 2001). In order to devise strategies for using collagen in the development of advanced biomaterials for biomedical engineering, it is typically desired to confer mechanical strength and resistance to enzymatic (collagenase) degradation resistance with chemical or physical cross-linking strategies. There are several strategies for cross-linking collagen-based biomaterials. Glutaraldehyde (GA) is the most widely used as a cross-linking agent for collagen-based biomaterials (Sheu et al., 2001; Barbani et al., 1995). However, GA and its reaction products are associated with cytotoxicity in vivo, due to the presence of cross-linking byproducts and the release of GA-linked collagen peptides during enzymatic degradation (Huang-Lee et al., 1990; van Luyn et al., 1992).

In order to avoid in vivo cytotoxicity and subsequent calcification of GA cross-linked collagen, several alternative compounds have been examined as potential collagen cross-linking agents (Khor et al., 1997; Sung et al., 1996) such as polyepoxy, hexamethylene diisocyanate (HMDI), 1-ethyl-3-(3-dimethylamino-propyl)carbodiimide (EDC), and ultraviolet (UV) or gamma-ray irradiation. Koob et al. recently described a process for cross-linking of type I collagen fibers with nordihydroguaiaretic acid (NDGA), a plant compound with antioxidant properties (Koob et al., 2002a; Koob et al., 2002b; Koob et al., 2001a; and Koob et al., 2001b). Koob et al. showed that NDGA significantly improved the mechanical properties of synthetic collagen fibers. In addition, they showed that NDGA cross-linked collagen fibers did not elicit a foreign body response nor did they stimulate an immune reaction during six weeks in vivo.

The extent of cross-linking and choice of cross-linking agent may also affect the porosity and pore size of the scaffold and may influence fibrous capsule thickness, blood vessel density, and the location of vessels within the three-dimensional porous scaffold (Joseph et al., 2004). Large pore scaffolds (greater than 60 micron pore size) allow deep penetration of capillaries and supporting extracellular matrix (ECM). Sharkawy et al., 1997 showed that after four weeks of subcutaneous implantation in rat, a well-organized collagen matrix typical of a foreign-body response encapsulated non-porous implants, while the porous polyvinyl alcohol (PVA) implants produced less fibrous and vascularized tissue capsules.

BRIEF SUMMARY OF THE INVENTION

Embodiments of the invention provide a biocompatible collagen covering for medical devices to provide improved biocompatibility and/or reduced risk of adverse reactions. Embodiments of the invention may be particularly suitable as coverings and/or scaffolds for chronically implantable medical devices.

Some embodiments are directed to non-degradable, biocompatible, three dimensional porous collagen scaffolds. These scaffolds can be formed or placed on and/or prepared around devices and/or sensors for implantation into a body. Some particular embodiments of the invention are implantable glucose sensors with a porous collagen scaffold on an external surface thereof. Sensors comprising a collagen scaffold of the invention can have improved biocompatibility by reducing tissue reactions while stimulating angiogenesis.

Other embodiments of the invention are directed to methods for preparing collagen scaffolds. Three dimensional porous collagen scaffolds can be fabricated by using a freeze-drying method and cross-linking them using different concentrations of at least one of glutaraldehyde (GA), 1-ethyl-3-(3-dimethylaminopropyl)carbodiimide (EDAC) and/or nordihydroguaiaretic acid (NDGA) solution.

One embodiment of the present invention concerns a biocompatible collagen scaffold and/or coating for use with a device implantable in the body or tissue of a person or animal, wherein said scaffold or coating comprises a polymer intercalated into said scaffold or coating.

One embodiment of the present invention also concerns a method for preparing a device for implantation into the body or tissue of a person or animal, said method comprising placing a biocompatible collagen scaffold or coating on said device wherein said scaffold or coating comprises a polymer intercalated into said scaffold or coating.

One embodiment of the present invention also concerns a method for providing an implantable device with a biocompatible collagen coating or scaffold, said method comprising:
 a) contacting an implantable device structure with a collagen containing solution;
 b) drying said collagen solution on said structure; and
 c) embedding said collagen of said structure in a polymer matrix.

One embodiment of the present invention also concerns a device having enhanced biocompatibility for implantation into the body or tissue of a person or animal, wherein said device comprises a biocompatible collagen scaffold and/or coating comprising a polymer intercalated into said scaffold or coating.

BRIEF DESCRIPTION OF THE DRAWINGS

FIG. 2C shows NDGA cross-linked collagen.

FIG. 3A shows a collagen scaffold with no cross-linking (200×; 25.0 kV); FIG. 3B shows a collagen scaffold with GA cross-linking (200×; 25.0 kV); and FIG. 3C shows a collagen scaffold with NDGA cross-linking (200×; 25.0 kV).

FIG. 6A shows NDGA cross-linked scaffold after two weeks collagenase treatment (200×; (25.0 kV); FIG. 6B shows GA cross-linked scaffold after two weeks collagenase treatment (200×; (25.0 kV); FIG. 6C shows NDGA cross-linked scaffold after four weeks collagenase treatment (200×; (25.0 kV); FIG. 6D shows GA cross-linked scaffold after four weeks collagenase treatment (200×; (25.0 kV).

FIGS. 7A-7G are digital photographs that show in vivo stability of GA and NDGA cross-linked scaffolds in rat subcutaneous tissue. FIGS. 7A-7C: two weeks after implantation; FIG. 7A shows NDGA cross-linked scaffold; FIG. 7B shows GA cross-linked scaffold; FIG. 7C-1 shows NDGA cross-linked scaffold; and FIG. 7C-2 shows GA cross-linked scaffold. FIGS. 7D-7G: four weeks after implantation; FIG. 7D shows NDGA cross-linked; FIG. 7E shows GA cross-linked scaffold; FIG. 7F shows NDGA cross-linked scaffold; and FIG. 7G shows GA cross-linked scaffold.

FIGS. 8A-8D are light microscope digital pictures of the implantable glucose sensing element (FIG. 8A shows uncoated sensor; FIG. 8B shows sensor coated with scaffold) and SEM morphology (FIG. 8C shows surface; FIG. 8D shows cross-section) of the scaffold region.

FIGS. 12A-12F show GA cross-linked scaffolds: FIG. 12A (3 days); FIG. 12B (7 days); FIG. 12C (14 days); FIG. 12D (21 days); FIG. 12E (28 days); FIG. 12F (49 days). FIGS. 12G-12L show NDGA cross-linked scaffolds: FIG. 12G (3 days) FIG. 12H (7 days); FIG. 12I (14 days); FIG. 12J (21 days); FIG. 12K (28 days); FIG. 12L (49 days). There is less inflammation associated with the NDGA cross-linked scaffold.

FIGS. 16A-16B show the hydrated collagen scaffold. FIG. 16A is GA cross-linked collagen scaffold and FIG. 16B is the NDGA-reinforced collagen scaffold.

FIG. 19A shows a detached implanted long-wire glucose sensor with NDGA reinforced collagen scaffold. FIG. 19B shows a stable implanted short-wire glucose sensor with NDGA reinforced collagen scaffold. FIG. 19C shows an implanted short- and/or long-wire glucose sensor with GA cross-linked collagen scaffold.

FIG. 20A shows GA cross-linked scaffolds (after two weeks implantation); FIG. 20B shows NDGA cross-linked scaffolds (after two weeks implantation).

Figure 1:
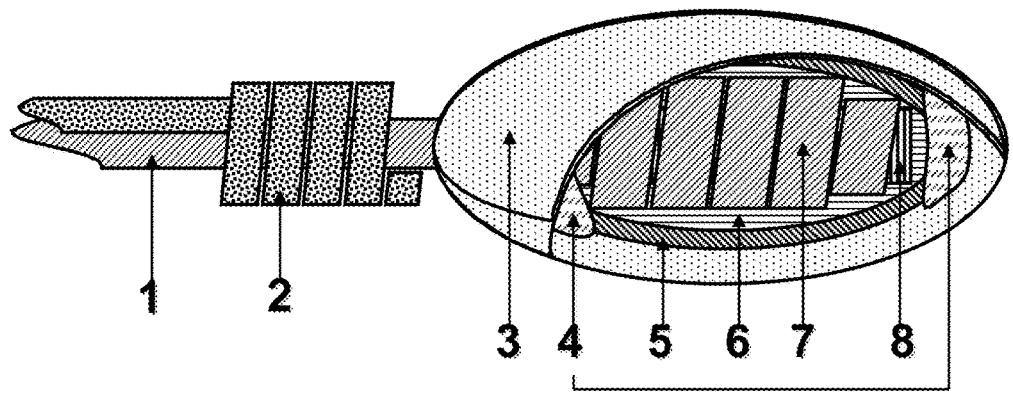
FIG. 1 is a schematic diagram of an exemplary scaffold-coated sensing element of a glucose electrode according to embodiments of the present invention
Figure 2A:
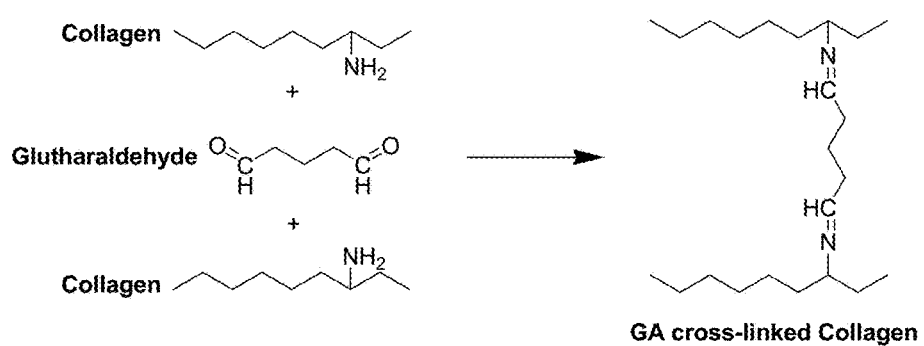
FIGS. 2A-2C are schematic illustrations of a chemical mechanism for GA (FIG. 2A) and NDGA (FIG. 2B) cross-linking of a collagen scaffold according to embodiments of the present invention.
Figure 2B:
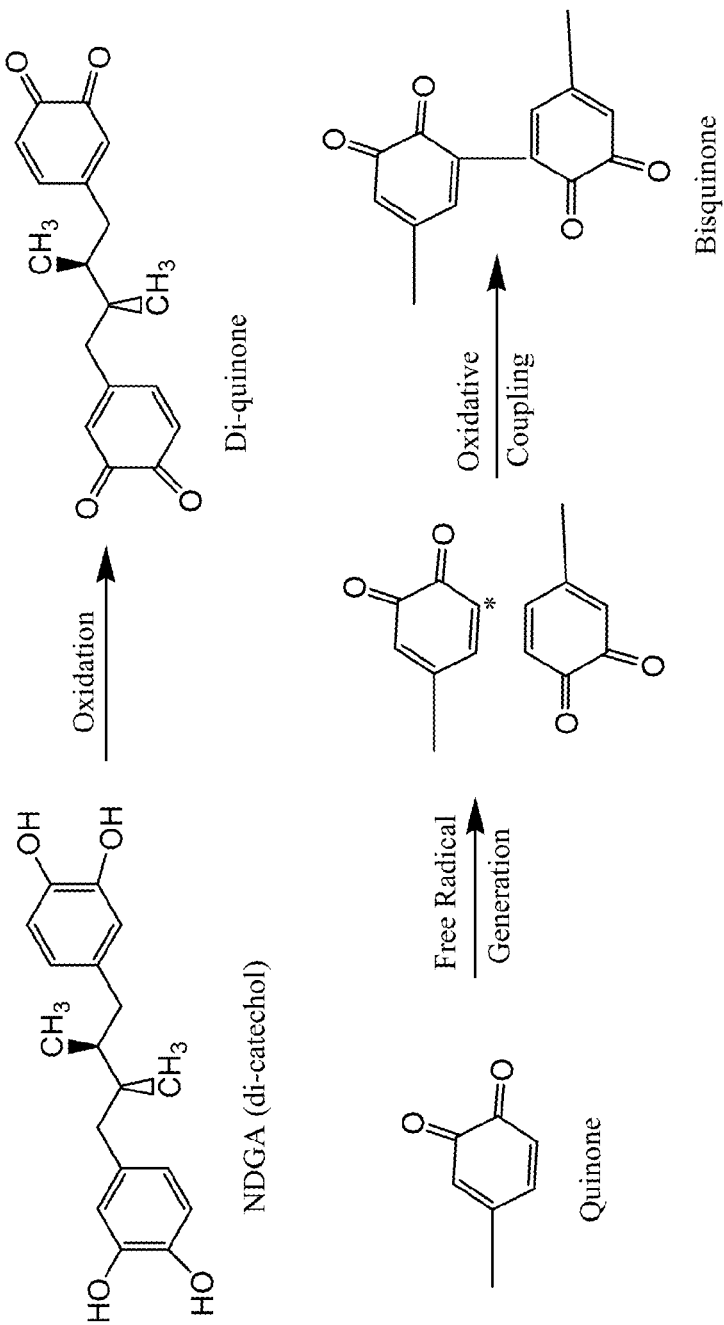
Figure 2C:
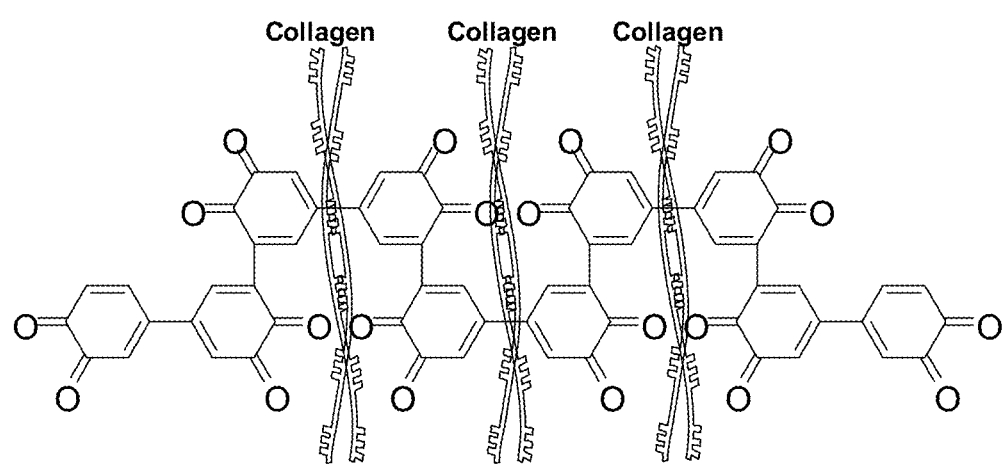

Further features, advantages and details of the present invention will be appreciated by those of ordinary skill in the art from a reading of the figures and the detailed description of the embodiments that follow, such description being merely illustrative of the present invention.

DETAILED DESCRIPTION OF THE INVENTION

Generally stated, embodiments of the subject invention are directed to collagen coverings, coatings and/or scaffolds which are particularly suitable for implantable medical devices, and methods of making and using the same in animal or human patients. The patient can be a human or other animal, such as a primate, equine, bovine, ovine, canine, or feline animal. The coatings, coverings and/or scaffolds can be provided as a tissue-contacting surface which may encapsulate all or a portion of the implantable devices to thereby provide a reduced immunogenic response and/or long-lived in vivo functionality of the implanted device.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y". As used herein, phrases such as "from about X to Y" mean "from about X to about Y".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "implantable" means the device can be inserted, embedded, grafted or otherwise acutely or chronically attached or placed on or in a patient. The term "tissue" means skin, muscle, bone or other group of cells. The term "chronically" means that the device is configured to remain implanted for at least 2 months, typically at least 6 months, and in some embodiments, one or more years while remaining operational for its intended function. The terms "coating" or "covering" refer to a material on a target surface of the device. The coating can be a porous coating that can inhibit cell and tissue fouling of the underlying device. The coating may not promote tissue growth. The coating can be a thin or thick film, foam or other barrier to tissue fouling and biodegradation. The term "scaffold" refers to a porous material and/or structure into which cells, tissue, vessels, etc . . . , can grow into, colonize and populate. The scaffold can inhibit cell and tissue fouling of the device and/or reduce foreign body inflammatory and immunogenic responses thereby prolonging the functional lifetime of the indwelling device.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber. Of course, synthetic collagen fibers can include non-collagenous components, such as hydroxyapatite or drugs that facilitate tissue growth. For example, the compositions can contain growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. Of course, synthetic collagen fibers can include non-collagenous components, such as particulates, hydroxyapatite and other mineral phases, or drugs that facilitate tissue growth. For example, the compositions can contain carbon nano-tubes, zinc nano-wires, nano-crystalline diamond, or other nano-scale particulates; larger crystalline and non-crystalline particulates such as calcium phosphate, calcium sulfate, apatite minerals. For example, the compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin.

Examples of devices that can benefit from the collagen coatings and/or scaffolds contemplated by embodiments of the invention, include, but are not limited to, implantable stents, including cardiac, arterial, neuro (brain), urinary, and other stents, implantable power generators (IPGs), pacemakers, defibrillators, cardioverters, stimulators and/or lead systems for the brain, central nervous system (CNS) or peripheral nervous system, cardiac or other biological system, cardiac replacement valves, implantable sensors including glucose sensors, cardiac sensors, identity or tracking sensors (e.g., RFID), sensors to detect or measure $O_2$, pH, temperature, ions, and the like, orthopedic implants, including tissue implants, such as facial implants for the chin, cheek, jawbone, and nose, implantable subcutaneous or percutaneous access ports, drain tubes such as Eustachian drain tubes, catheters such as urinary catheters, respiratory-assist tubes, and the like.

The collagen scaffold or covering of fibers can be configured to substantially encase the target implantable device or may cover only a portion thereof.

The scaffold or covering can be a three dimensional array of fibers or fibrils held together or on the device in any suitable manner including by their natural affinity to stick together upon compression or extrusion, by using a sticky coating or adhesive, such as a gelatinous coating, or by otherwise attaching the fibers to form the array. The scaffold or coverings may also optionally comprise extruded, electrospun, braided and/or mesh collagen segments. The term "braided" and derivatives thereof mean to (inter)weave and/or interlock in any manner, three or more fibers or bundles of fibers together, including knitting and knotting and combinations of these or other interlocking constructions. The collagen can be provided as laminate fibers, foams, electrospun yarns or other formations.

In some embodiments, the scaffold or covering can be configured as a drug delivery device for short term or long-term release or elution. For example, hydrogel matrices may be integrated into or on the collagen scaffold or covering.

In some embodiments, an NDGA treated collagen scaffold or collagen coating is applied to a biosensor or other implantable medical devices. The collagen scaffold or coating of the invention improves biocompatibility and longevity of sensors and devices implanted in a body or tissue. The use of collagen scaffold and/or coating of embodiments of the present invention reduces the effect of tissue reactions (i.e., inflammation and fibrosis) on implanted biosensors and medical devices.

In some embodiments, a non-degradable three-dimensional porous collagen scaffold is provided around an implantable glucose sensor to substantially encapsulate at least a portion of the device to improve its biocompatibility by reducing tissue reactions while also stimulating angiogenesis and inhibiting biofouling. FIG. 1 illustrates one example of a glucose sensor (1—Teflon-covered Pt—Ir wire; 2—Ag/AgCl reference wire; 3—collagen scaffold; 4—electrically-insulating sealant; 5—Epoxy-Pu outer membrane; 6—enzyme layer; 7—stripped and coiled Pt—Ir wire; 8—cotton fiber with GOD gel). Examples of glucose sensors have been described in published U.S. Patent Application No. 20070131549 and U.S. Pat. Nos. 6,475,750; 6,033,866; 6,965,791; and 6,893,545.

The three dimensional porous collagen scaffold can be provided in any suitable manner. In some embodiments, the scaffold can be prepared by using a freeze-drying method and reinforced using a nordihydroguaiaretic acid (NDGA) solution.

The subject invention also concerns biosensors and other devices comprising a biocompatible collagen scaffold. In particular embodiments, the device comprises a sensor, such as a glucose sensor. Sensors can be, but are not limited to electrochemical, optical, acoustic, piezoelectric, or thermoelectric sensors. In some embodiments, the collagen scaffold is treated to form a polymer that intercalates into the collagen scaffold, for example as is described in U.S. Pat. Nos. 6,821,530 and 6,565,960. In some embodiments, the collagen scaffold is treated with a cross-linking compound comprising a reactive catechol at a pH sufficient to produce a reactive quinone. Typically, the pH used in the reaction is neutral or alkaline. In one embodiment, the pH is between 7 to about 8. In another embodiment, the pH is between about 8 to about 9, or about 9 to about 11. In a specific embodiment, the reactive catechol used for cross-linking is a di-catechol. In an exemplified embodiment, a collagen scaffold is embedded in an NDGA bisquinone polymer matrix. The device can also comprise an epoxy or other protective material layer. In some embodiments, the epoxy layer is under the collagen scaffold. The device can also comprise an electrically insulating layer. In some embodiments, the electrically insulating layer is under the collagen scaffold. Collagen scaffolds of the present invention can comprise open pores from about 10 µm to about 200 µm in diameter, or from about 20 µm to 100 µm in diameter. In some embodiments, the collagen scaffold of the invention has a mean pore size of about 60 µm or less in diameter. In some embodiments, the collagen scaffold has a mean pore size of between about 40 µm and about 80 µm. As noted above, the collagen scaffolds can be loaded with various therapeutic compounds, such as compounds that have antimicrobial activity, and/or that modulate inflammatory responses, angiogenesis, etc. In some embodiments, the collagen scaffold is loaded with antimicrobial, anti-inflammatory, and/or angiogenic compounds, drugs or growth factors.

Figure 21:
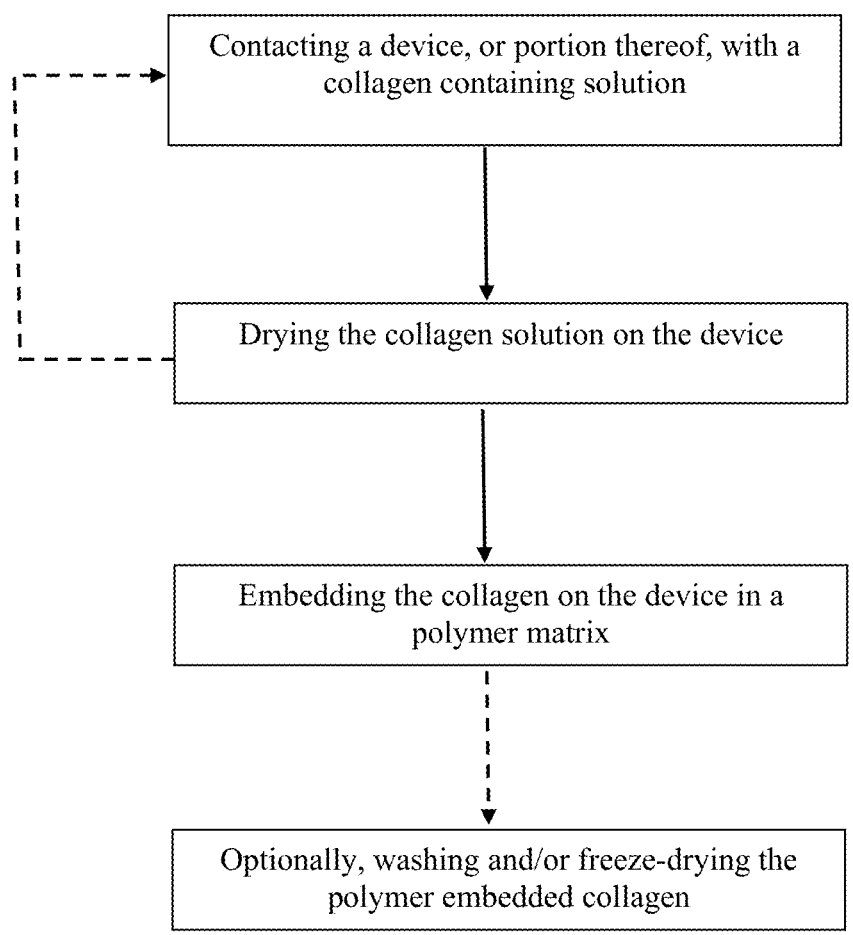
FIG. 21 shows a flow chart for a method for preparing a device according to the present invention comprising a biocompatible collagen scaffold. Dashed lines indicate optional steps.

Embodiments of the subject invention also concern methods for preparing a device for implantation into the body or tissue or animal wherein a biocompatible collagen scaffold of the present invention is prepared around the exterior of at least a portion of the device. Optionally, the device or a portion thereof is coated with an epoxy layer, such as epoxy-polyurethane and/or an electrically insulating layer. In some embodiments, the method comprises contacting the device with a collagen containing solution, followed by drying the collagen solution on the device, and then cross-linking and/or embedding the collagen in a polymerized matrix. In some embodiments, the collagen containing solution comprises between about 0.5% to about 10% (w/v) collagen, and typically about 1% (w/v) of collagen. In some embodiments, the collagen containing solution is prepared in an acidic solution. The drying steps can be by freeze-drying. The steps of contacting the device with a collagen solution, then drying the collagen solution can be repeated multiple times. In one embodiment, the steps are repeated about 2 to 4 times. In a specific embodiment, the collagen can be embedded in a polymer matrix using a reactive catechol at a pH sufficient to produce a reactive quinone that can polymerize to form a polymer. In some embodiments, the reaction solution for the reactive catechol is treated so as to increase the levels of dissolved oxygen in the solution, such as by sparging the solution with oxygen. Typically, the pH used in the reaction is neutral or alkaline. In one embodiment, the pH is between 7 to about 8. In another embodiment, the pH is between about 8 to about 9, or about 9 to about 11. In an exemplified embodiment, the reactive catechol is a di-catechol, such as NDGA. The collagen coated device can be exposed to a solution of NDGA at a neutral or alkaline pH for a suitable period of time (e.g., 24 hours). The collagen scaffold is thereby embedded in an NDGA bisquinone polymer matrix. The scaffold can be optionally washed following NDGA treatment. In some embodiments, after the collagen is treated to embed the collagen in polymerized matrix, the embedded collagen is subsequently freeze-dried. Optionally, the method can include loading a collagen scaffold with a compound, drug, growth factor, etc. that has antimicrobial, anti-inflammatory, and/or angiogenic activity. A flow chart of some embodiments of the subject methods is shown in FIG. 21.

In some embodiments, the device is a biosensor having for example, a nucleic acid, a protein, an organic compound or other molecule attached, coupled, or cross-linked thereto (for example, an enzyme can be attached to an electrode of the sensor). Sensors can be used to detect glucose, alcohols, amino acids, drugs (and metabolites thereof), urea, hormones, and other compounds and analytes of interest. Sensors contemplated by the present invention include, but are not limited to, sensors that can detect microorganisms, proteins, nucleic acids, organic compounds, such as sugars and fatty acids, and other molecules or analytes.

As shown in FIG. 1, in an exemplified embodiment, the glucose sensor is a coil-type glucose sensor comprising a cross-linked enzyme, such as glucose oxidase. In one embodiment, the scaffold on the exterior of the device comprises open pores of about 10 µm to about 200 µm in diameter (mean), or from about 20 µm to about 100 µm in diameter. In a specific embodiment, the mean pore size of the collagen scaffold around the exterior of the device has a mean pore size of about 60 µm or less in diameter. In one embodiment, the mean pore size of the collagen scaffold is between about 40 µm and about 80 µm in diameter. The sensor can also optionally comprise layers, such as an epoxy layer, and an electrically insulating layer. Collagen scaffolds of the invention can be loaded with various compounds that modulate inflammatory responses, angiogenesis, etc. In one embodiment, a collagen scaffold is loaded with antimicrobial, anti-inflammatory, and/or angiogenic drugs or growth factors.

The subject invention also concerns methods for monitoring biological processes in vivo using a device of the invention that comprises a biocompatible collagen scaffold of the invention. In some embodiments, the device is a glucose sensor that can be used to monitor blood sugar levels in a patient, such as a diabetic patient. In another embodiment, the device is a sensor that can detect hormone levels in a person or animal, such as hormones associated with pregnancy. In other embodiments, the device is a cardiac or nervous system monitor for monitoring heart, brain, etc. functions. In an exemplified embodiment, a device of the invention is implanted into the body or tissue of a person or animal and the biological process that the device is capable of monitoring or detecting, etc. is monitored or detected. Biological processes can be monitored using the subject device for weeks, months, or years with the scaffold or coating providing resistance to biofouling thereby promoting operational longevity in vivo.

The subject invention also concerns the use of collagen scaffolds of the invention for the in vitro or in vivo delivery of bioactive compounds, drugs, growth factors, proteins, peptides, nucleic acids, inorganic or organic molecules, etc. A collagen scaffold of the invention can be loaded with a bioactive compound, etc. and then the loaded scaffold can be implanted or contacted with the body, tissue, cells, etc. of a person or animal. The compounds are then permitted to be released from the scaffold into the body, tissue, cell, etc. The collagen scaffold can be provided on a biodegradable or non-degradable support structure or matrix.

The collagen used in the present invention can be synthetic or derived from any suitable animal species. The collagen can be from a vertebrate animal or an invertebrate (e.g., starfish, sea urchin, sponges, etc.). In some embodiments, the collagen is fish, shark, skate, or ray collagen. In another embodiment, the collagen is human, equine, bovine, ovine, porcine, canine, or feline collagen. In an exemplified embodiment, the collagen is bovine collagen.

Collagen scaffolds of the present invention are stable both in vitro and in vivo for at least 4 weeks at body temperature. Also, scaffold application around glucose sensors did not significantly affect the sensor's sensitivity. Scaffolds of the present invention can be used to deliver anti-inflammatory drugs and angiogenic growth factors (e.g., VEGF, PDGF) in order to create a controlled local tissue environment around sensors with minimum inflammation and fibrosis but with increased blood vessel density.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

MATERIALS AND METHODS

Materials

Type I collagen (purified from fetal bovine tendon) was a generous gift from Shriners Hospital for Children (Tampa, Fla.). Nordihydroguaiaretic acid (NDGA) was purchased from Cayman Chemical Co. (Ann Arbor, Mich.). Glucose, bovine serum albumin (BSA) and 50% (w/w) glutaraldehyde (GA) were obtained from Fisher Scientific (Pittsburgh, Pa.). Glucose oxidase (GOD) (EC 1.1.3.4., Type X-S, *Aspergillus niger*, 157,500 U/g), epoxy adhesive (ATACS 5104), polyurethane (PU), tetrahydrofuran (THF) and collagenase (EC 3.4.24.3, Type I, from *Clostridium histolyticum*, 302 U/mg) were obtained from Sigma-Aldrich (St. Louis, Mo.). Sprague-Dawley out-bred rats (male, 375-399 g) were purchased from Harlan (Dublin, Va.).

Preparation and Cross-Linking of Collagen Scaffold

The collagen scaffolds were prepared by a freeze-drying method. Collagen was dissolved in 3% acetic acid to prepare a 1% (w/v) solution. The solution was applied to a cylinder-shaped polypropylene mold (Φ10 mm, height 8 mm) and then freeze-dried. A cylindrical three dimensional porous scaffold was obtained. The scaffolds were then cross-linked with NDGA or GA to minimize solubility and improve resistance to collagenase degradation.

For NDGA cross-linking, dried collagen scaffolds were briefly soaked in absolute ethanol, followed by soaking in 2 M of NaCl solution for 12 h at room temperature. Scaffolds were re-suspended in oxygen sparged phosphate buffered saline (PBS, 0.1 M $NaH_2PO_4$, pH 9.0) for 30 min at room temperature. Scaffolds were then treated with 3 mg of NDGA in 1 mL of PBS as follow: NDGA was dissolved in 0.4 N NaOH at a concentration of 30 mg/mL. One milliliter of the NDGA solution was added directly to PBS in which the scaffolds were suspended to a final concentration of 3 mg/mL. The scaffolds were agitated in the NDGA solution for 24 h at room temperature. The scaffolds were removed, briefly rinsed with water and freeze-dried.

For a comparative study of the effectiveness of the NDGA treatment, other scaffolds were treated with 0.5% GA for 2 h or 12 h in ethanol solution at room temperature. To prevent the dissolution or loss of the matrix during the GA cross-linking process, 100% ethanol was used instead of water. The cross-linked scaffolds were washed with de-ionized water and freeze-dried again. The morphology of the scaffolds before/after cross-linking was examined using scanning electron microscopy (SEM) after gold sputter coating of the samples in a metal evaporator according to standard procedures.

To evaluate the stability of the scaffold after cross-linking, the degree of cross-linking (Dc) was estimated by weighing the dried samples before and after cross-linking. Dc was calculated using the following equation:

$$Dc\ [\%] = (\text{sample mass after cross-linking/sample mass before cross-linking}) \times 100$$

The swelling property of the porous scaffolds was examined by measuring water absorption. The scaffolds were weighed after thorough drying ($W_{dry}$) and immersed in purified water. After 24 h, the scaffolds were removed from the water and immediately weighed again ($W_{wet}$). Water absorption was calculated by using the following equation:

$$\text{Water absorption (\%)} = [(W_{wet} - W_{dry})/W_{wet}] \times 100$$

In Vitro and In Vivo Evaluation of the Collagen Scaffolds

In order to examine the biological stability of the cross-linked scaffolds, in vitro and in vivo biodegradation tests were performed. In vitro biodegradation of NDGA and GA cross-linked scaffolds was tested using bacterial collagenase. Fabricated NDGA and GA cross-linked collagen scaffolds were incubated in the collagenase solution (1 mg/mL in PBS at 37° C.) for up to 4 weeks. Scaffolds were removed from the solution, rinsed with de-ionized water and freeze-dried at given time intervals (weeks 1 to 4) during incubation. The in vitro degradation was evaluated as the percentage of weight difference of the dried scaffold before and after enzyme digestion.

In order to determine the stability of the cross-linked scaffolds in vivo, NDGA and GA cross-linked collagen scaffolds were directly implanted in rats. The scaffolds were disinfected with 70% ethanol solution for 2 h and implanted subcutaneously in the back of the rats. Scaffolds were explanted at 7, 14, 21, and 28 days after implantation. After explantation, the scaffolds were examined macroscopically.

Preparation of Porous Collagen Scaffolds Around Implantable Glucose Sensors

Coil-type glucose sensors loaded with cross-linked enzyme (GOD: Glucose Oxidase) were fabricated using a Platinum-Iridium (Pt/Ir) wire (Teflon coated, Φ0.125 mm, Pt:Ir=9:1, Medwire, Sigmund Cohn Corp., Mount Vernon, N.Y.). Then, bovine tendon type I collagen scaffolds were applied around the sensors (FIG. 1). Briefly, in order to fabricate a glucose sensor, the Teflon coating of the top 10 mm of a Pt/Ir wire was removed and the wire was wound up along a 30-gauge needle to form a coil-like cylinder. The cylinder unit had an outer diameter of 0.55 mm and an inner diameter of 0.3 mm and a length of 1 mm. A cotton thread was inserted inside the coil chamber to retain the enzyme solution during enzyme coating of the electrodes. GOD was added and cross-linked to the sensors by dip coating in an aqueous solution containing 1% GOD, 4% BSA, and 0.6% (w/w) glutaraldehyde. The outer membrane of the sensor was coated with Epoxy-Polyurethane (Epoxy-PU) by dipping in Epoxy-PU solution (2.5% (w/v) in THF, Epoxy:PU=1:1). The sensor was dried at room temperature for at least 24 h. The two ends of the sensing element were sealed by electrically-insulating sealant (Brush-On electrical tape, North American Oil Company) (Long et al., 2005; Yu et al., 2006).

To apply collagen scaffolds around the sensors, the sensors were dip-coated with 1% (w/v) collagen solution and freeze-dried. The porous scaffolds around the glucose sensors were cross-linked with either NDGA or GA as previously described. Obtained sensors were stored dry at room temperature or in PBS at 4° C. The morphology of the sensors was observed using light microscope and SEM.

Silver wires (Teflon coated, Φ0.125 mm, World Precision Instruments, Inc.) were used to fabricate the Ag/AgCl reference electrodes. Silver wires were coiled and anodized galvanostatically at 1 mA overnight in stirred 0.1 M HCl (Long et al., 2005; Yu et al., 2006).

In Vitro Characterization of Sensors Coated With Scaffolds

The glucose sensors were characterized in PBS (pH 7.4) at 700 mV versus the incorporated Ag/AgCl reference electrodes. The working electrode (Pt/Ir wire) and Ag/AgCl reference electrode of each sensor were connected to an Apollo 4000 potentiostat (World Precision Instruments, Inc., Sarasota, Fla.). The background current was allowed to stabilize for 10 minutes, and the sensors were then exposed to a series of glucose solutions in order to examine their sensitivities and linearities. The response sensitivity (S) was repeatedly assessed by 1) measuring the response current ($I_1$) of a $C_1$ glucose solution, 2) adding a concentrated glucose solution into the measured solution to increase the glucose concentration to $C_2$ and 3) measuring the response current ($I_2$) of the resulting solution. The sensitivity was expressed as the current increase caused by a 1 mM glucose increase, i.e. $S=(I_2-I_1)/(C_2-C_1)$.

In Vivo Anti-Inflammation Effect of the NDGA-Crosslinked Scaffold

Figure 4:
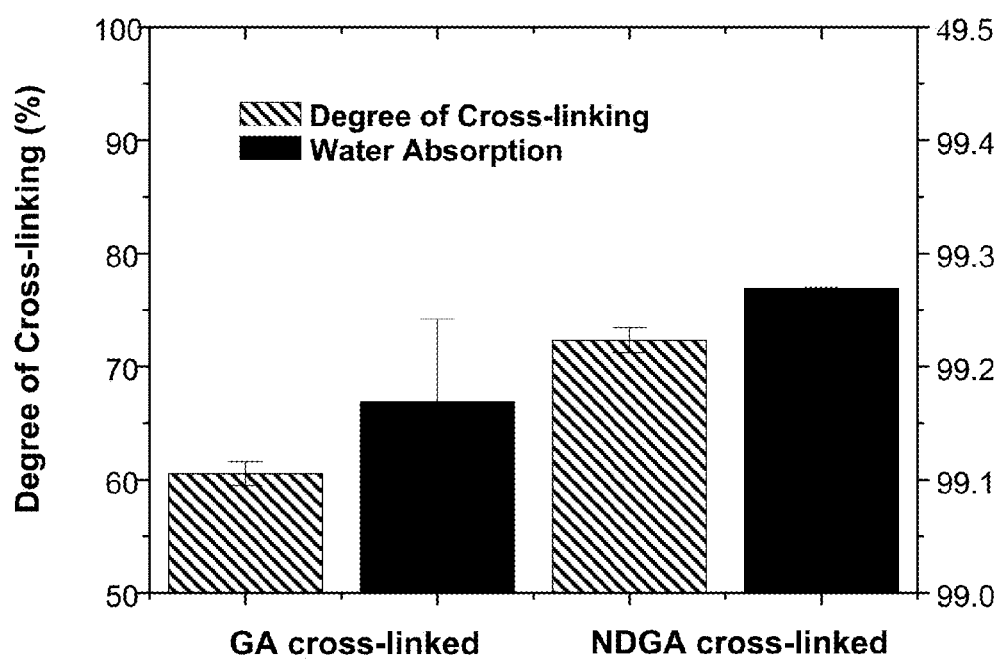
FIG. 4 is a bar graph of degree (%) of cross-linking and degree (%) of water absorption of GA and NDGA cross-linked scaffolds that shows bulk properties of GA and NDGA cross-linked scaffolds according to embodiments of the present invention. Results are shown as means±SD (n=3).

To evaluate in vivo anti-inflammatory effect of the NDGA-crosslinking, NDGA and GA-(control) crosslinked scaffolds were implanted subcutaneously in the back of the Sparague-Dawley rats. The subcutaneous tissue samples around the implanted site were explanted 3-, 7-, 14-, 21-, 28-, and 49-days post implantation. At set time intervals, tissue samples were collected and fixed in situ (10% buffered formalin). The fixed tissue samples were embedded in paraffin and sectioned with 10 μm thickness. Various sections were stained with hematoxylin and eosin (H&E) and imaged using microscope with digital camera. FIG. 4 shows the inflammation response associated with implanting a biosensor according to the invention.

EXAMPLE 1

Preparation of Porous Cross-Linked Collagen Scaffolds

Figure 7A:
Figure 7B:
Figures 1, 2, 7C:
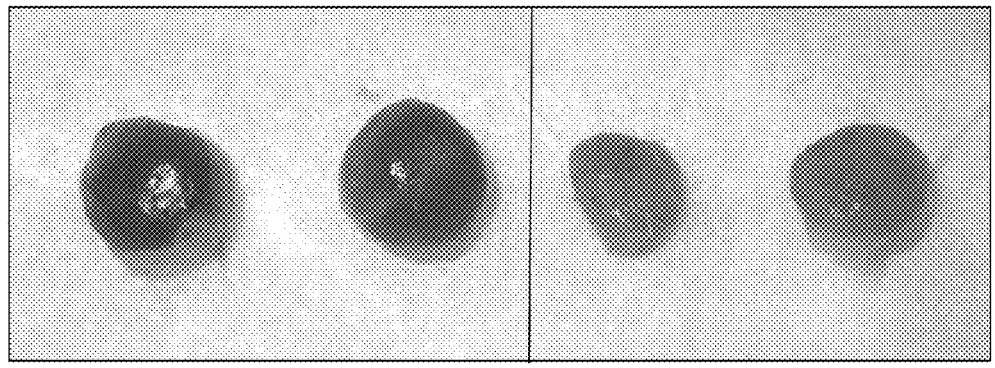
Figure 7D:
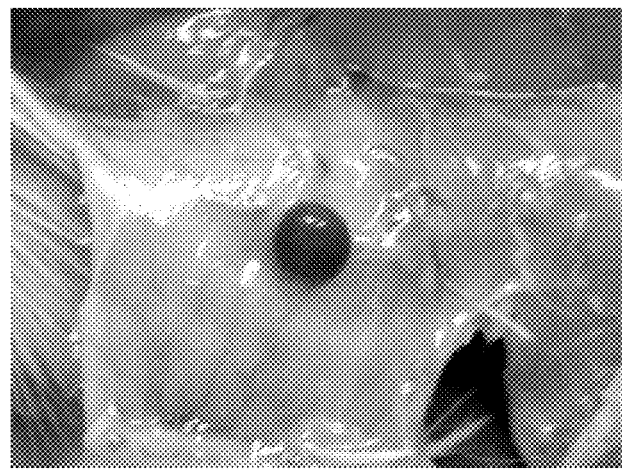
Figure 7E:
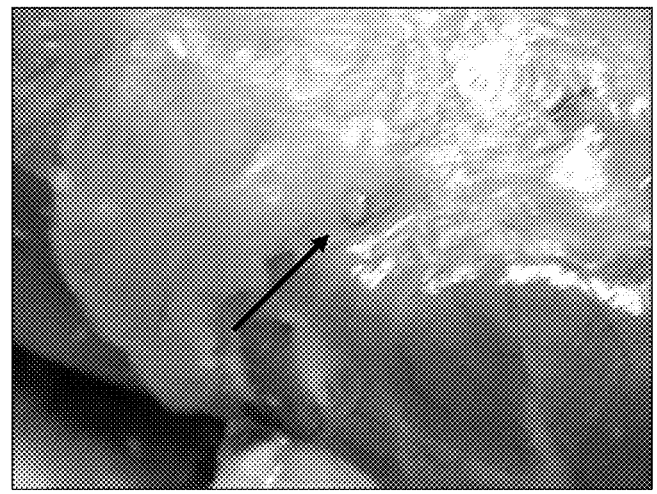
Figures 7F, 7G:
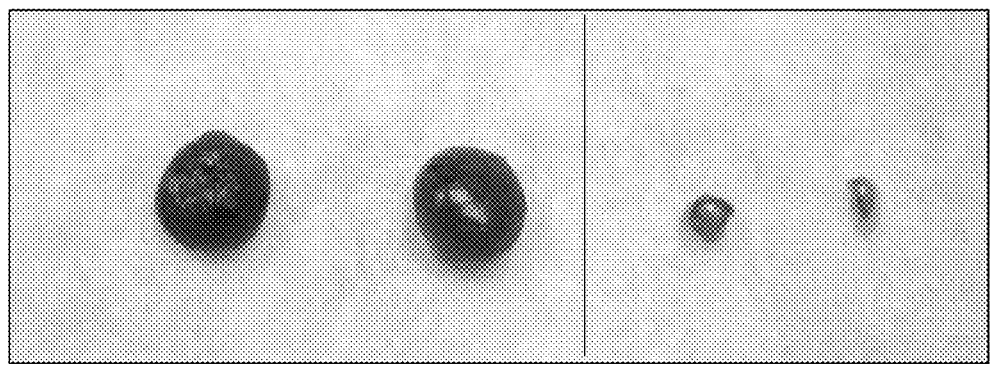

The chemistry of the NDGA cross-linking reaction differs from the reaction using the GA treatment (FIG. 2). GA is the most common cross-linking agent used for fixation of collagen scaffolds for tissue bioengineering. Both aldehyde functional groups of the GA molecule react with amine groups between two neighboring polypeptide chains, particularly lysine side chains. Unfortunately, GA cross-linking is encumbered with potential cytotoxicity problems caused by the presence of unreacted residual groups and/or the release of monomers and small polymers during enzymatic degradation (Huang-Lee et al., 1990; van Luyn et al., 1992).

NDGA is an alternative cross-linking agent which possesses reactive catechols. Collagen cross-linking with NDGA mimics the quinine tanning mechanism in the skate egg capsule. Catechol-quinone tanning systems are prevalent in a wide variety of animals, which the process serves to strengthen vulnerable extracellular matrices (e.g. insect cuticle, mussel byssus threads) (Koob et al., 2002a; Koob et al., 2004). NDGA, isolated from the creosote bush, is a low molecular weight di-catechol containing two ortho-catechols. The two catechols on NDGA undergo auto-oxidation at neutral or alkaline pH producing reactive quinones. Two quinones then couple via aryloxy free radical formation and oxidative coupling, forming bisquinone crosslinks at each end. The NDGA continues forming a large cross-linked bisquinone polymer network in which the collagen fibrils are embedded. The NDGA treatment can also form crosslinks with amino acid side chains of collagen (Koob et al., 2002a; Koob et al., 2002b; Koob et al., 2004).

Figure 3A:
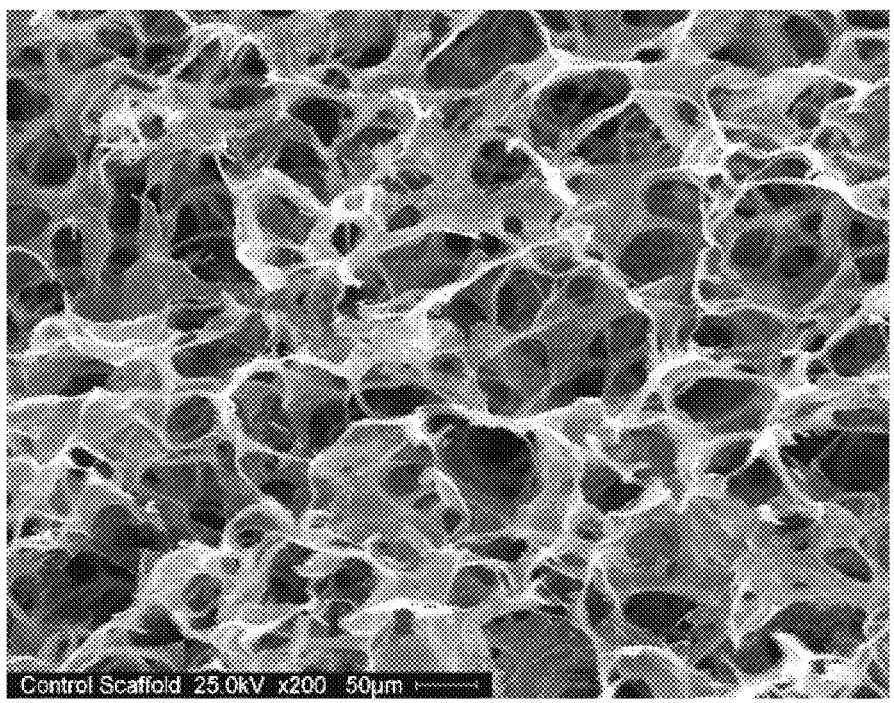
FIGS. 3A-3C are scanning electron micrographs (SEM) which show SEM morphology of exemplary collagen scaffolds according to embodiments of the invention. Determination of the pore size of collagen scaffolds by SEM.
Figure 3B:
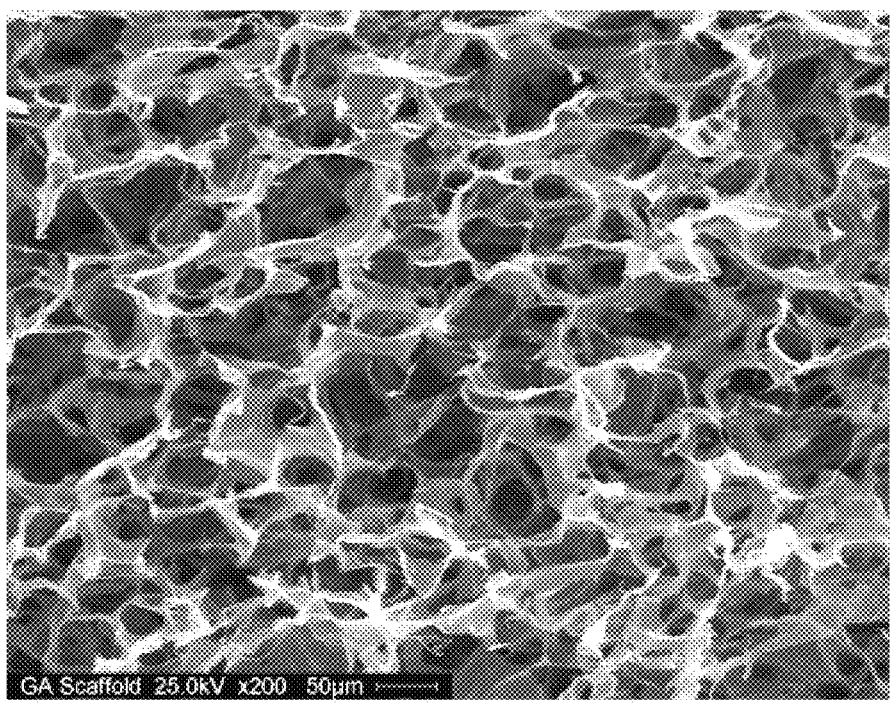
Figure 3C:
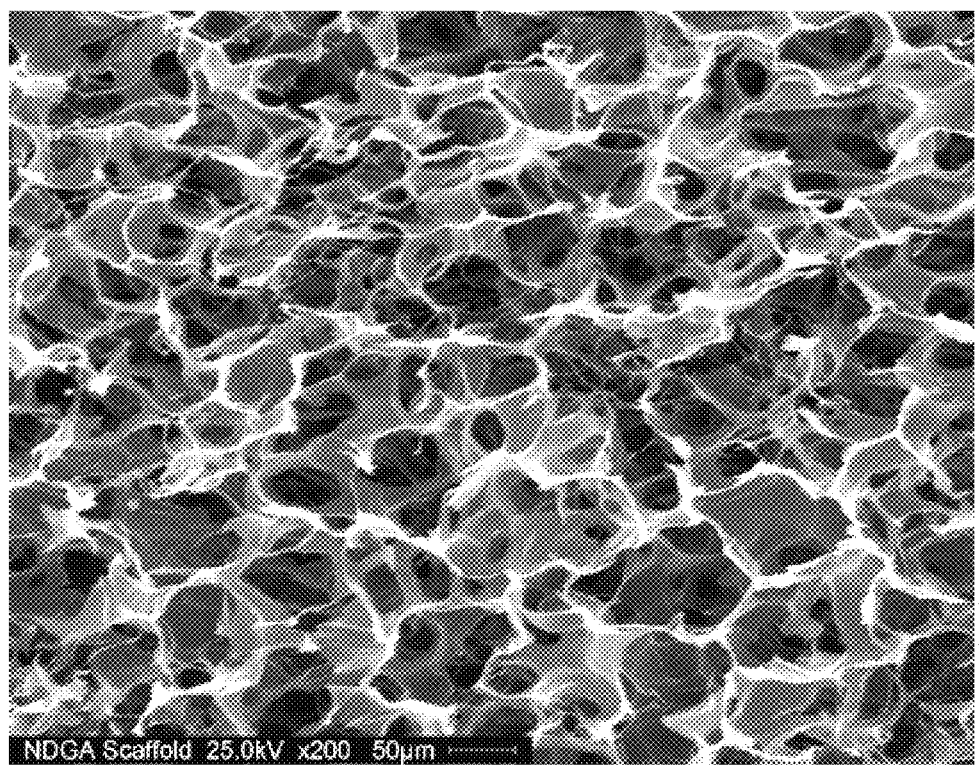

In this study, highly porous collagen scaffolds were prepared by a freeze-drying method. It was ascertained that the scaffolds prepared as described herein have an open cell and interconnected pore structure based on SEM observation (FIG. 3A). The pores of the scaffolds are regularly distributed and range from 20 to 100 μm in diameter (mean ~60 μm). Sharkawy et al., 1997 reported that the a 60 μm mean-pore-sized polyvinyl alcohol (PVA) sponge provided a tissue in-growth environment and allows for infiltration of neovasculature but did not allow for fibrous tissue ingrowth. After cross-linking with NDGA and GA, the pore size and pore structure of both scaffolds are not significantly altered (FIG. 3B and FIG. 3C). FIG. 4 shows the degree of cross-linking and water absorption of the scaffolds using different cross-linking methods. The mass was reduced to about 70% after NDGA treatment and 60% with GA treatment after the cross-linking process due to the loss of uncross-linked collagen components. Cross-linked collagen scaffolds had a significantly higher form stability than uncross-linked collagen scaffolds. Also, the swelling behavior of both NDGA and GA cross-linked scaffolds showed no significant differences between the two different cross-linking agents. The water absorptions of both cross-linked scaffolds were above 99%. The high swelling property of sponge-like matrices seems to be dependent on the porous inner structure of the scaffold, which possesses good absorbent characteristics (Patel et al., 1996).

EXAMPLE 2

In Vitro and In Vivo Evaluation of Porous Collagen Scaffolds

Figure 5:
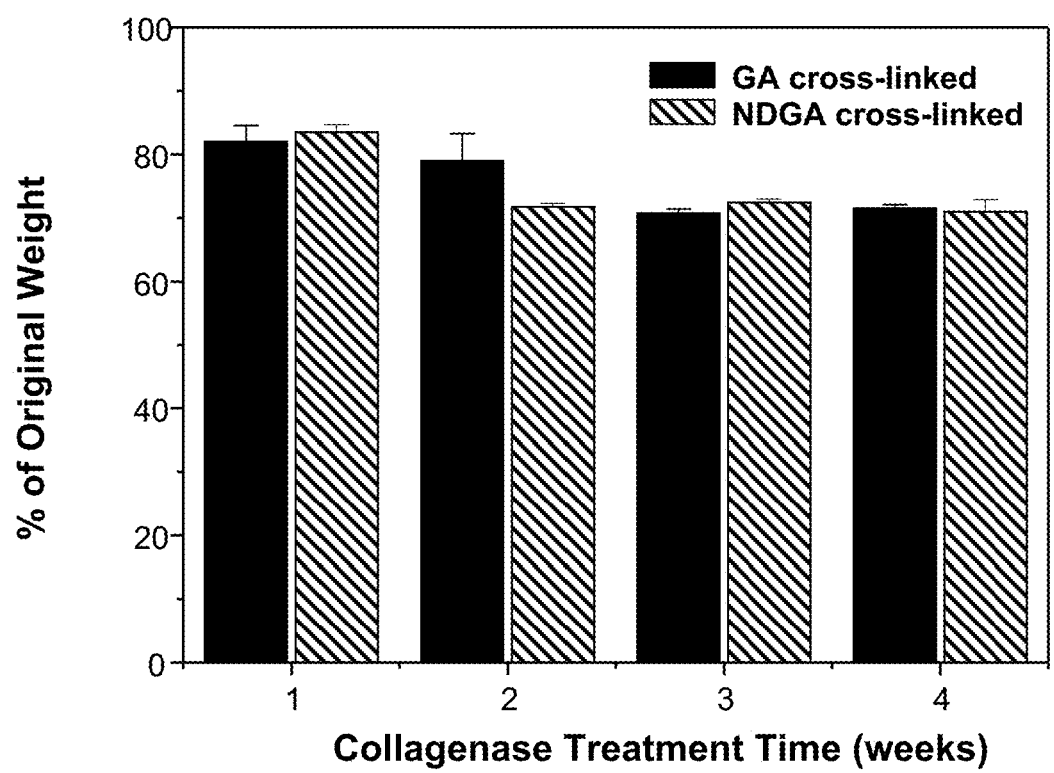
FIG. 5 is a bar graph of % (original weight) verses collagenase treatment time (weeks) that shows collagenase resistance of GA and NDGA cross-linked scaffolds in vitro. Results are shown as means±SD (n=3).

The biological stability of the cross-linked collagen scaffolds was investigated by in vitro and in vivo biodegradation tests. Degradation in both uncross-linked (control) and cross-linked scaffolds was characterized by determining weight loss of the scaffold after enzymatic digestion. The uncross-linked scaffolds and scaffolds cross-linked with GA for 2 hours were completely degraded in the collagenase solution within several hours while NDGA or GA cross-linked (for 12 h) scaffolds were not degraded within 24 hours. A significant increase in resistance to enzymatic digestion could be shown after cross-linking. FIG. 5 shows long-term collagenase in vitro degradation test (weight remaining %) of the NDGA and GA cross-linked scaffolds.

Figure 6A:
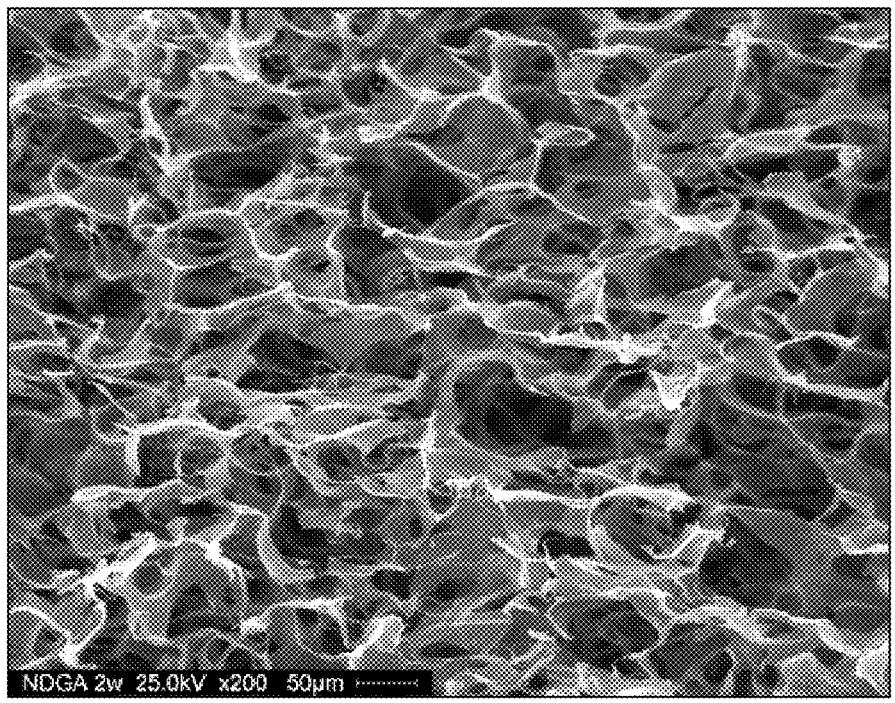
FIGS. 6A-6D are SEMs that show SEM morphology of the scaffold after in vitro degradation study.
Figure 6B:
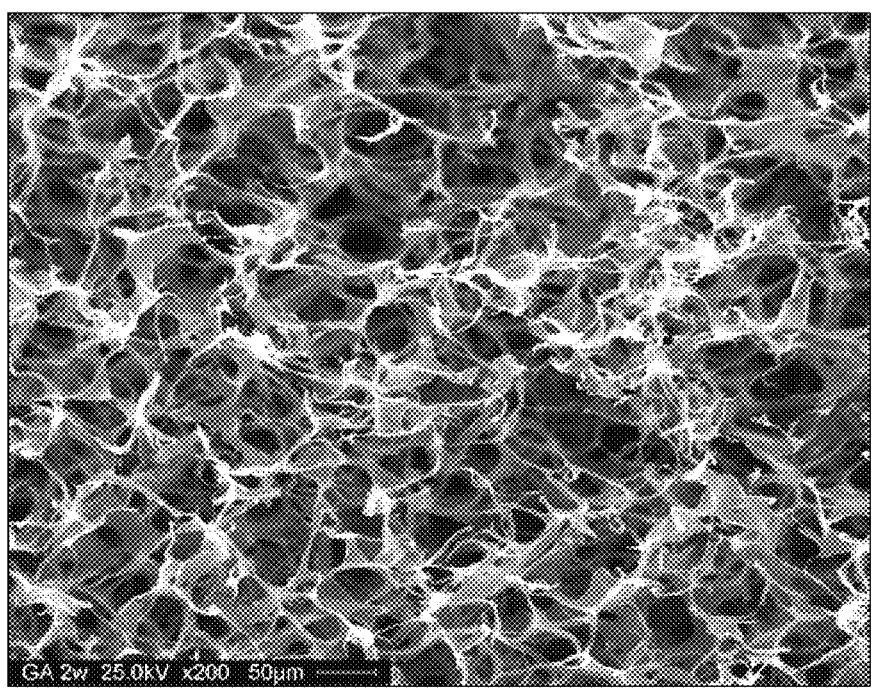
Figure 6C:
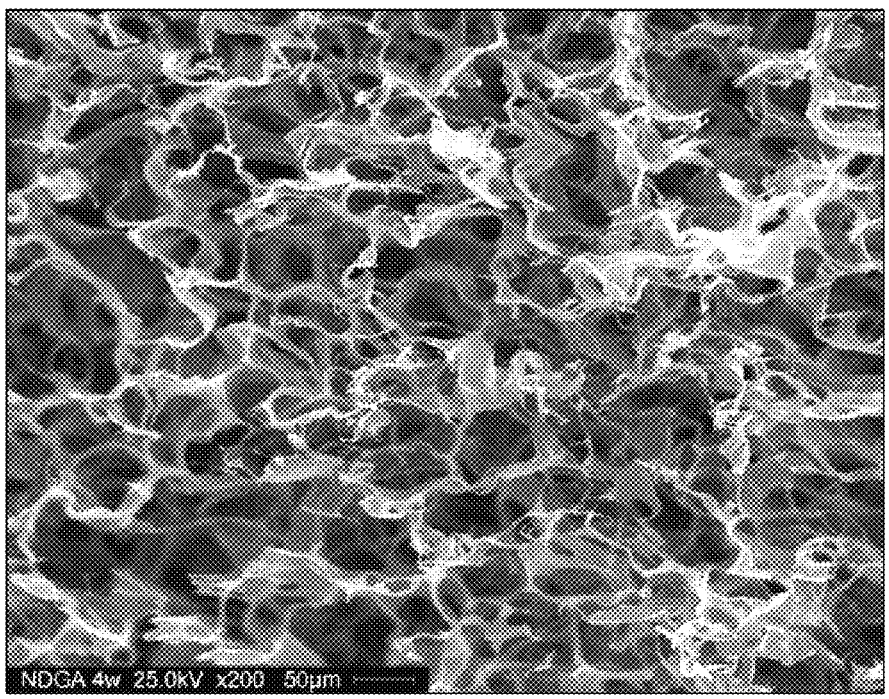
Figure 6D:
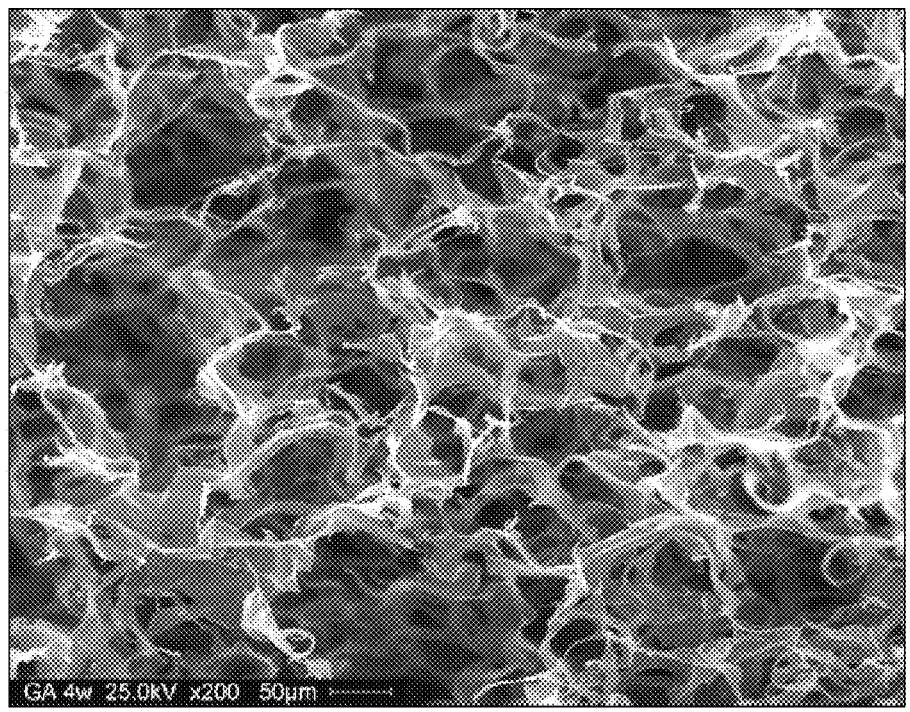

After one week exposure to collagenase, both types of scaffolds showed high resistance to enzymatic digestion (>80% weight remaining). After three and four weeks, all scaffolds retained 70% of their initial mass. However, in the case of GA cross-linked scaffold, the pore size was increased after 4 weeks collagenase digestion process (FIG. 6B vs FIG. 6D). In contrast, the pore size of NDG scaffolds did not appear to increase (FIG. 6A and FIG. 6C). This result suggests that NDGA or GA treatment can provide collagen scaffolds with improved enzymatic biodegradation stability. The collagenase cleavage sites were more effectively blocked by the cross-linking of the collagen scaffolds (Angele et al., 2004).

In order to study the stability of the cross-linked scaffolds in vivo, cross-linked collagen scaffolds were implanted in the subcutaneous tissue of the Sprague-Dawley rats and explanted samples two and four weeks post implantation. After two weeks implantation, the NDGA cross-linked scaffolds did not show evidence of physical damage, but the overall shape of the GA cross-linked scaffolds was deformed and the size slightly reduced (FIG. 7A). After four weeks, the size and shape of the GA cross-linked scaffolds were dramatically changed but there was no significant change in NDGA cross-linked scaffolds (FIG. 7B). This indicated that NDGA treatment can much more improve the physical stability of the scaffolds in vivo than GA treatment, presumably because of greater mechanical properties of NDGA cross-linked collagen. Koob et al., 2002b tested NDGA cross-linked collagen fibers and reported that the ultimate tensile strength of NDGA cross-linked fibers were significantly greater than those of GA cross-linked fibers because NDGA dose not chemically crosslink the collagen unlike GA cross-linking. Instead, the collagen fibrils are embedded in a polymerized NDGA matrix, i.e., a fiber reinforced composite (FIG. 2).

EXAMPLE 3

Porous Collagen Scaffolds Around Implantable Glucose Sensors

Coil-type glucose sensors loaded with cross-linked enzyme (GOD: Glucose Oxidase) were first fabricated by using Platinum-Iridium (Pt/Ir) wires. Then, bovine tendon type I collagen scaffolds were applied around the sensors (FIG. 1). Yu et al., 2006 previously reported that this "coil-type" sensor allows more GOD loading, provides a larger electrochemical surface area, and therefore increases the response current as compared to a "needle-type" sensor. The coil-type sensor of the invention is flexible and miniaturized (0.5 mm dia.) for subcutaneous implantation. It is composed of a two-electrode system with a glucose indicating platinum electrode and a Ag/AgCl reference-counter electrode. A sensor of the present invention utilizes a three-layer membrane configuration of cross-linked collagen scaffold, epoxy-polyurethane (Epoxy-PU) and GOD. The collagen scaffold (the outer layer in this case) can uptake 99% of its dry weight of water including glucose and other molecules. The Epoxy-PU membrane under the scaffold is permeable to glucose and oxygen but impermeable to most interfering substances. GOD immobilized in a BSA/GA matrix is sandwiched between the Pt/Ir wire and the Epoxy-PU membrane. In order to eliminate air bubbles entrapped in the chamber during coating, to stabilize the enzyme gel inside the chamber, and to make the enzyme solution easier to remain in the coil, cotton fiber was used inside the coil chamber. The collagen scaffolds were prepared by a freeze-drying method and cross-linked to minimize water solubility and enzymatic collagenase degradation. A light microscope, was used to confirm that the porous scaffolds thoroughly surrounded the sensor tips (FIG. 8A and FIG. 8B). The surface and cross-sectional morphology of the scaffolds around the sensors were also observed using SEM. Many collagen fibrils and uniform open pore structure were observed on the surface (FIG. 8C). Inter-connected open pores in the scaffold and a thickness of 150-200 µm were observed in cross-sectional region (FIG. 8D).

Figure 9:
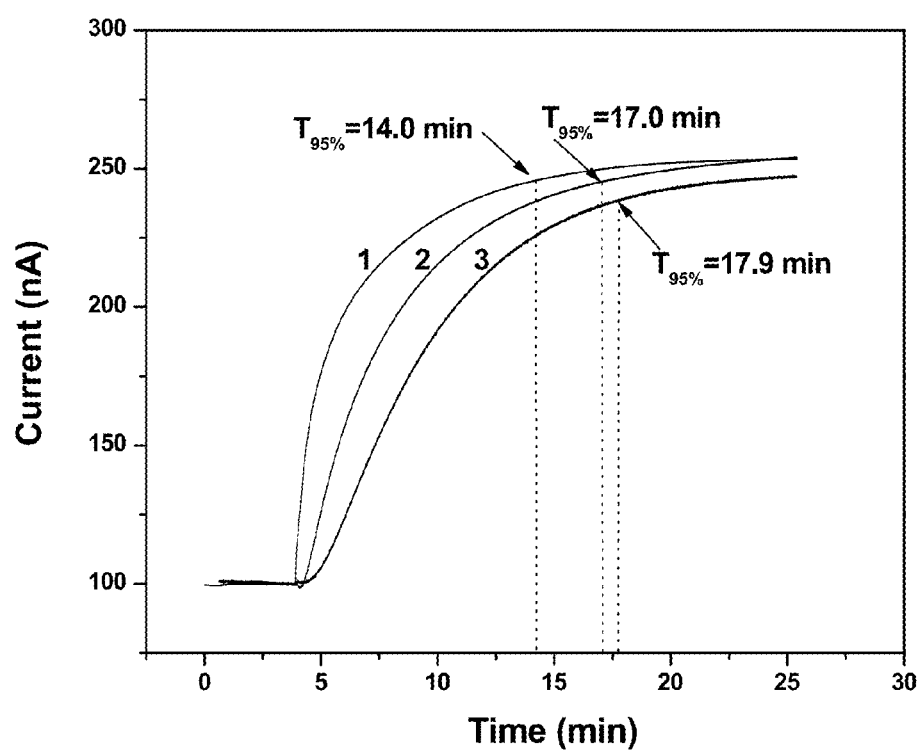
FIG. 9 is a graph of current (nA) versus time (minutes) that shows amperometric response curves of the glucose sensors (response curve 1—uncoated sensor; response curve 2—coated with GA cross-linked scaffold; and response curve 3—coated with NDGA cross-linked scaffold) from 5 mM to 15 mM glucose concentration. $T_{95\%}$, is defined as the time at 95% of the maximum current change $(I_{15\ mM} - I_{5\ mM})$.

The amperometric response curves of the glucose sensors with and without scaffold (control) were obtained by varying the glucose concentration from 5 mM to 15 mM as shown in FIG. 9. These glucose concentrations were selected because these concentrations were located in the linear response region (2-30 mM) of the studied sensors. The results showed no significant response current change before and after scaffold application around the sensor. However, the sensors with scaffolds had a slower response time to reach equilibrium current ($T_{95\%}$) than control sensors. The response time, $T_{95\%}$, is defined as the time at 95% of the maximum current change ($1_2$-$I_1$). The $T_{95\%}$ of control sensor was 14.0 min whereas $T_{95\%}$ of the sensors with NDGA- and GA cross-linked scaffold were 17.9 min and 17.0 min, respectively. The delay of the response time (17.9 and 17 min) was probably caused by the added physical barrier of the porous scaffolds.

Figure 10:
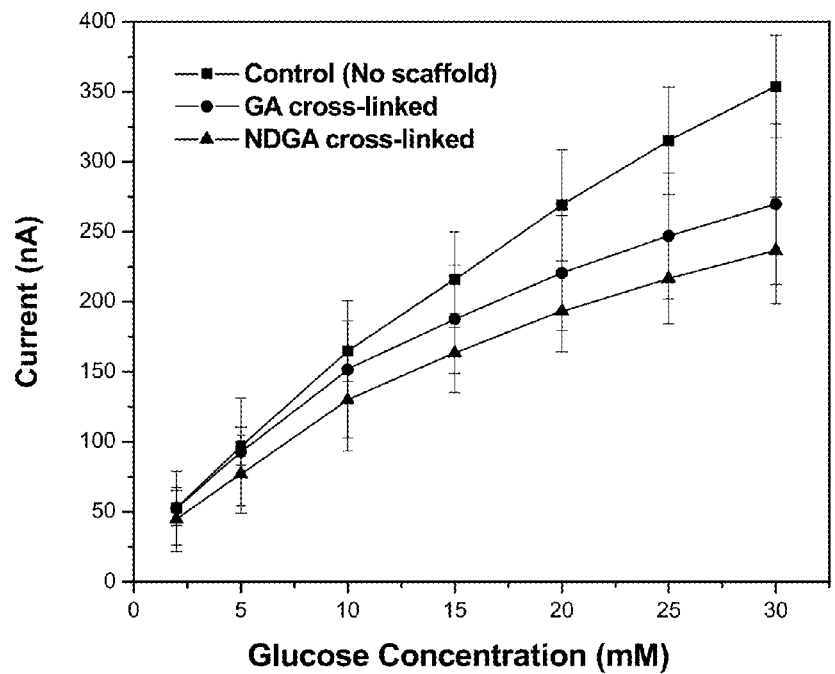
FIG. 10 is a graph of current (nA) versus glucose concentration (mM) that shows amperometric responses of uncoated and collagen scaffold-coated glucose sensors (2-30 mM glucose). The control (no scaffold) is shown by filled-in squares; GA cross-linked scaffold is shown by filled-in circles; NDGA cross-linked scaffold is shown by filled-in triangles. Results are shown as means±SD (n=3).

The currents produced by sensors with NDGA- and GA cross-linked scaffolds and by sensors without scaffolds in response to varying glucose concentration (2-30 mM) are shown in FIG. 10. The response currents of the control sensors in the high glucose concentration region (20-30 mM) were only a little higher than those of the sensors having scaffolds. The average sensitivity of the control, NDGA- and GA cross-linked scaffold around sensors was 11.0, 7.1, and 8.1 nA/mM, respectively. Therefore, scaffold application around the glucose sensors did not negatively affect the function of the sensors.

Figure 11:
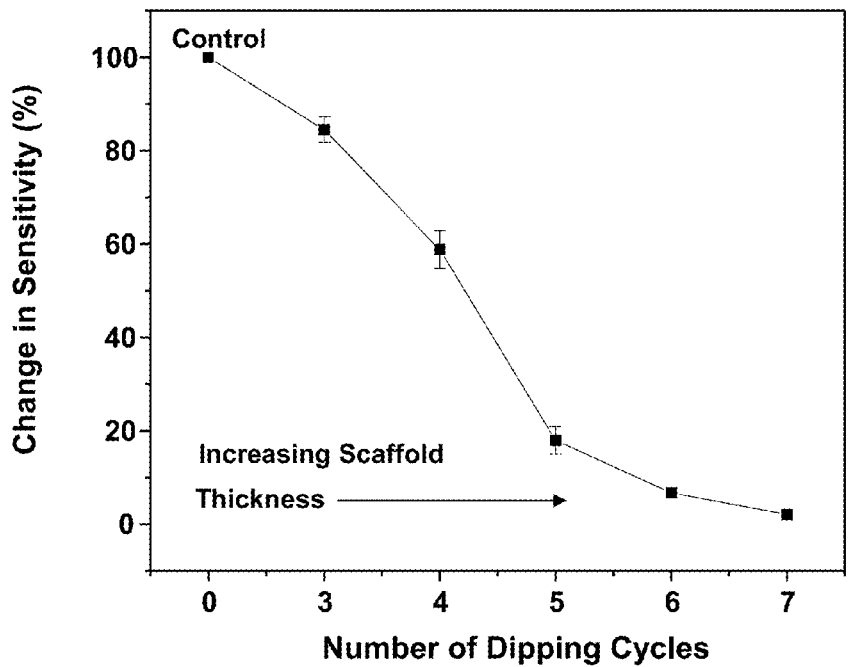
FIG. 11 is a graph of change in sensitivity (%) versus number of dipping cycles that shows the effect of the scaffold thickness on glucose sensor sensitivity. Results are shown as means±SD (n=3).
Figure 12A:
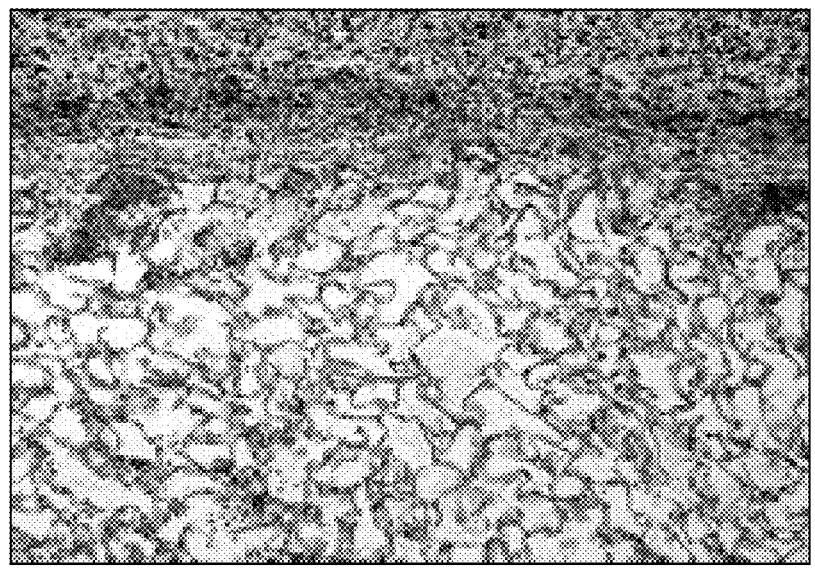
FIGS. 12A-12L are digital images taken over time showing the inflammation response (Direct implantation-Histological Assay) of biosensors.
Figure 12B:
Figure 12C:
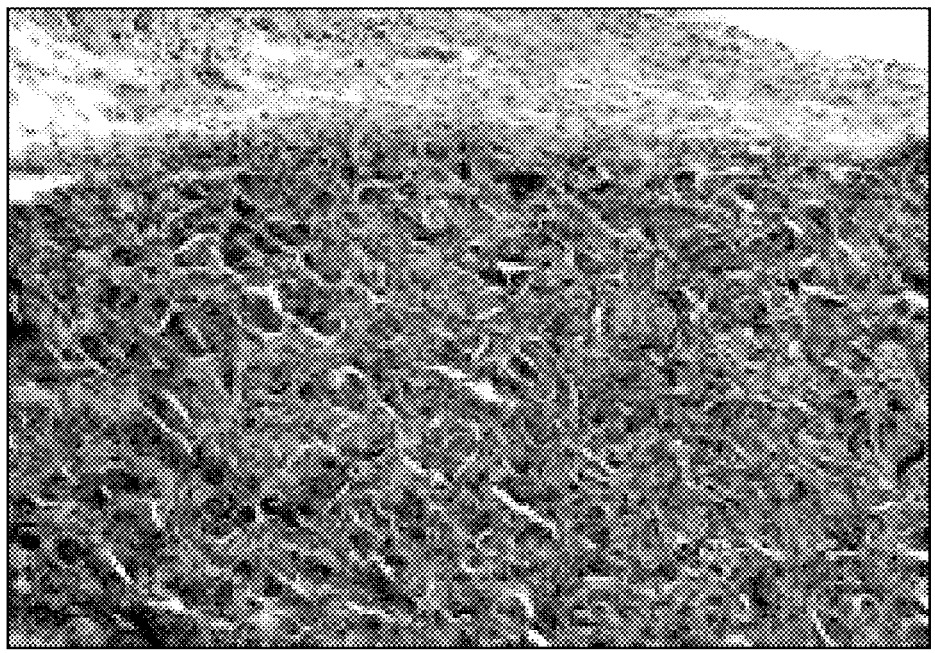
Figure 12D:
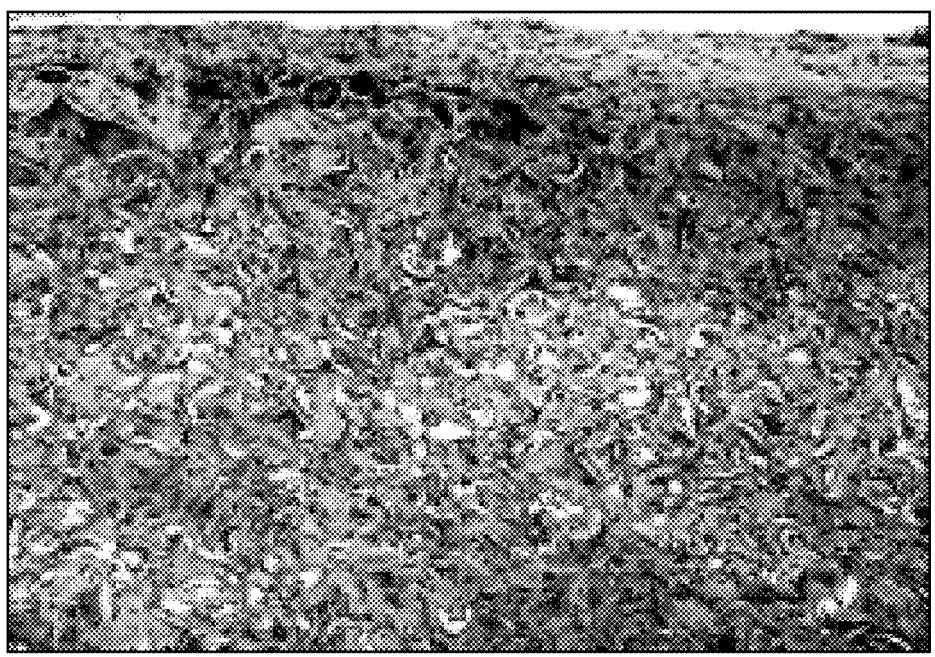
Figure 12E:
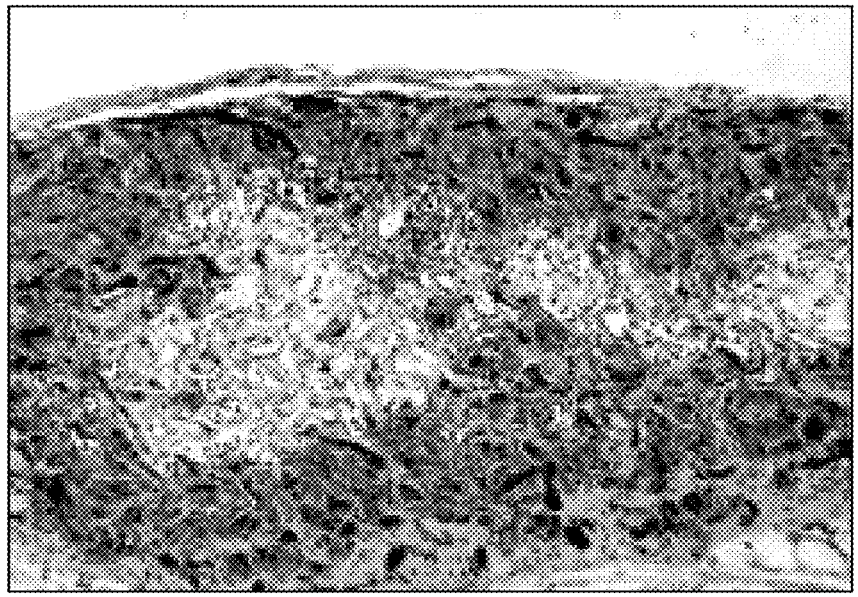
Figure 12F:
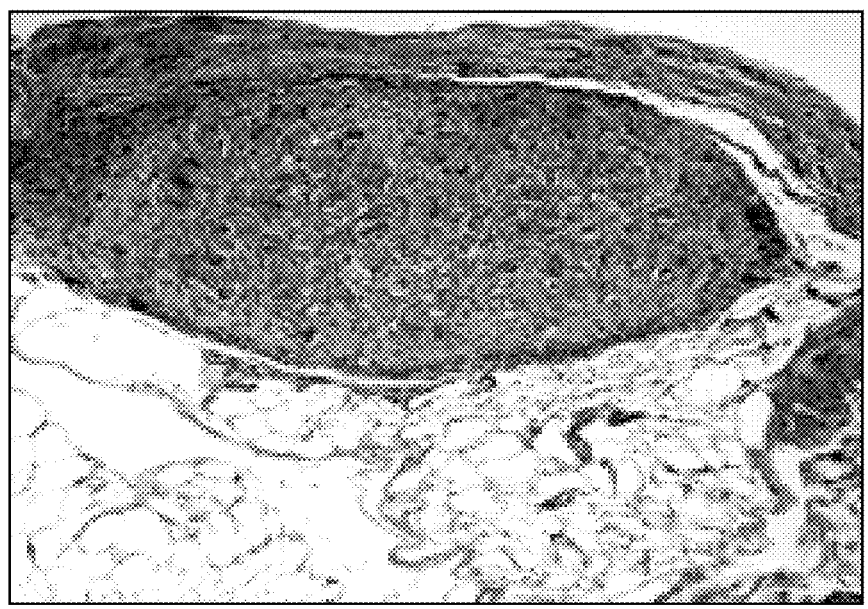
Figure 12G:
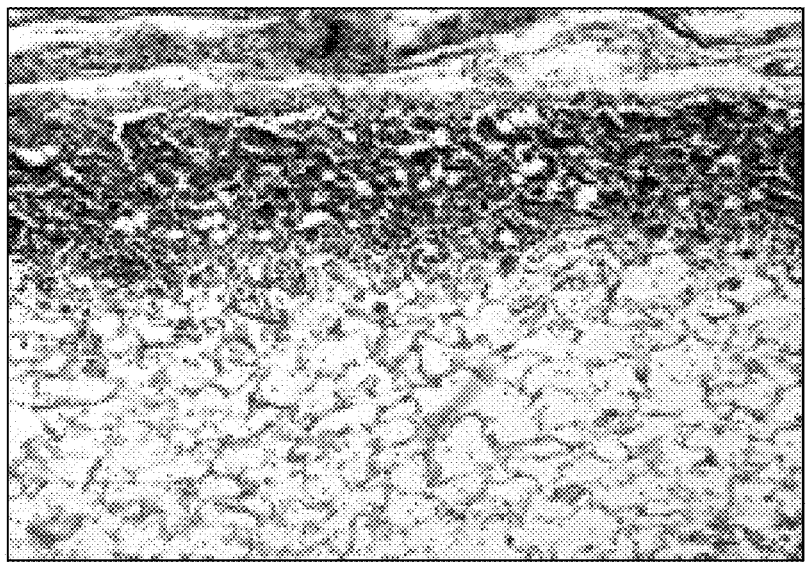
Figure 12H:
Figure 12I:
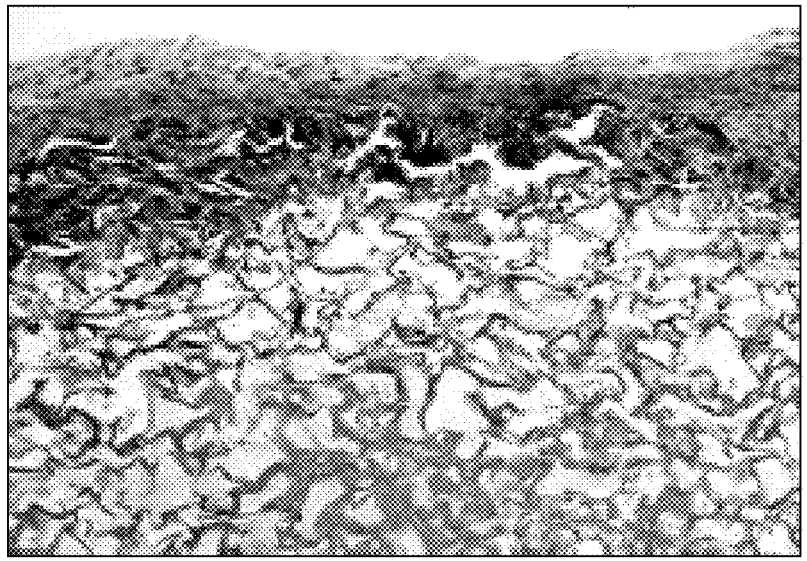
Figure 12J:
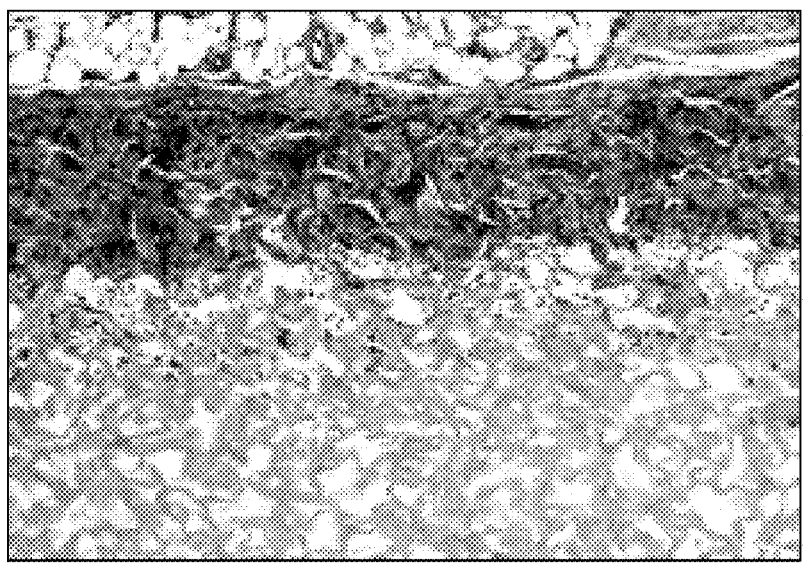
Figure 12K:
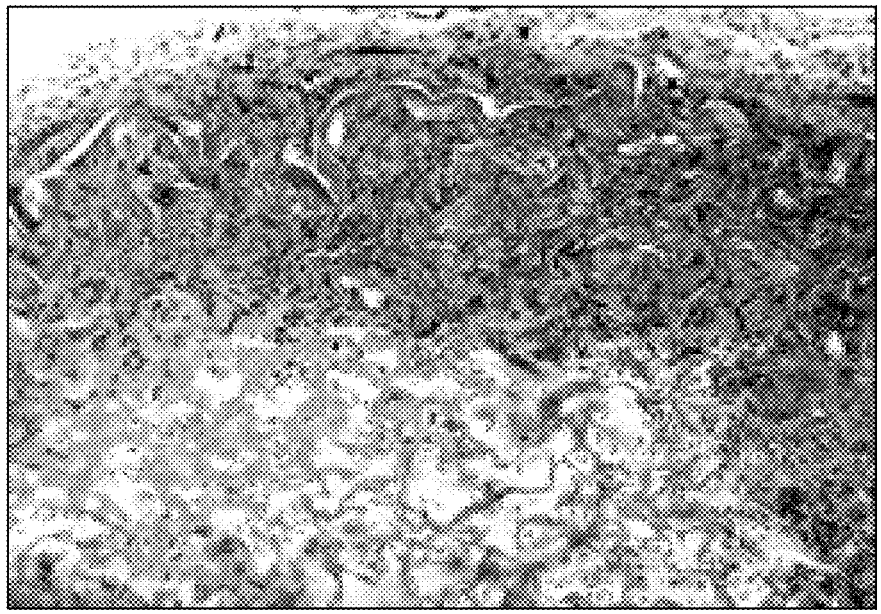
Figure 12L:
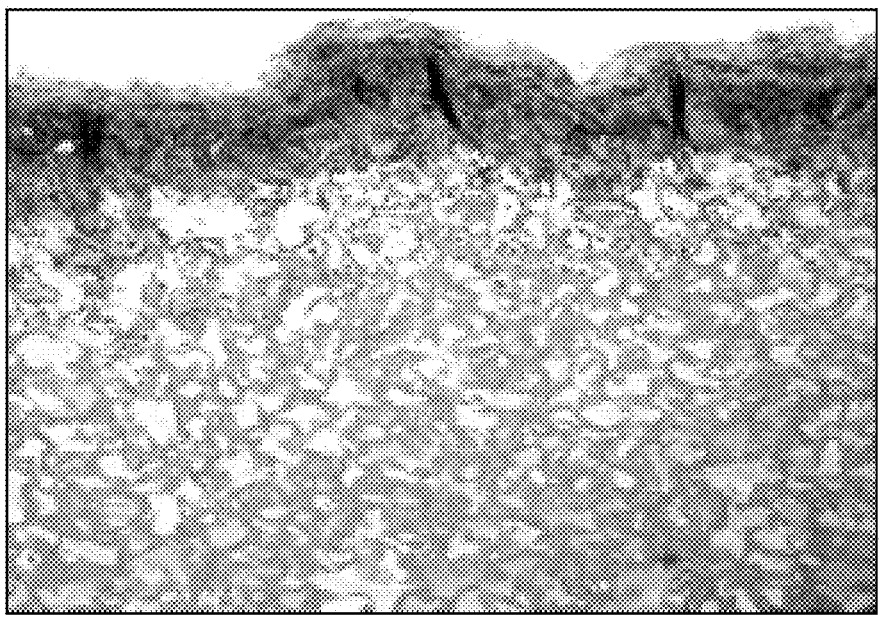

The sensitivity changes of the sensors with varying wall thickness of the scaffold controlled by dipping cycles in collagen solution were examined. As can be seen in FIG. 11, the sensitivity of sensors dip-coated four times remained at 60% of their initial sensitivity (i.e., without a scaffold layer). When the sensors were dip-coated more than 5 times, glucose could not diffuse properly through the scaffolds and the sensitivity was reduced to below 20% of the initial sensitivity. Although the porous scaffold material has good water absorbent properties, the wall thickness can affect the sensor function.

EXAMPLE 4

In Vitro and In Vivo Evaluation of Implantable Glucose Sensor

Figure 13:
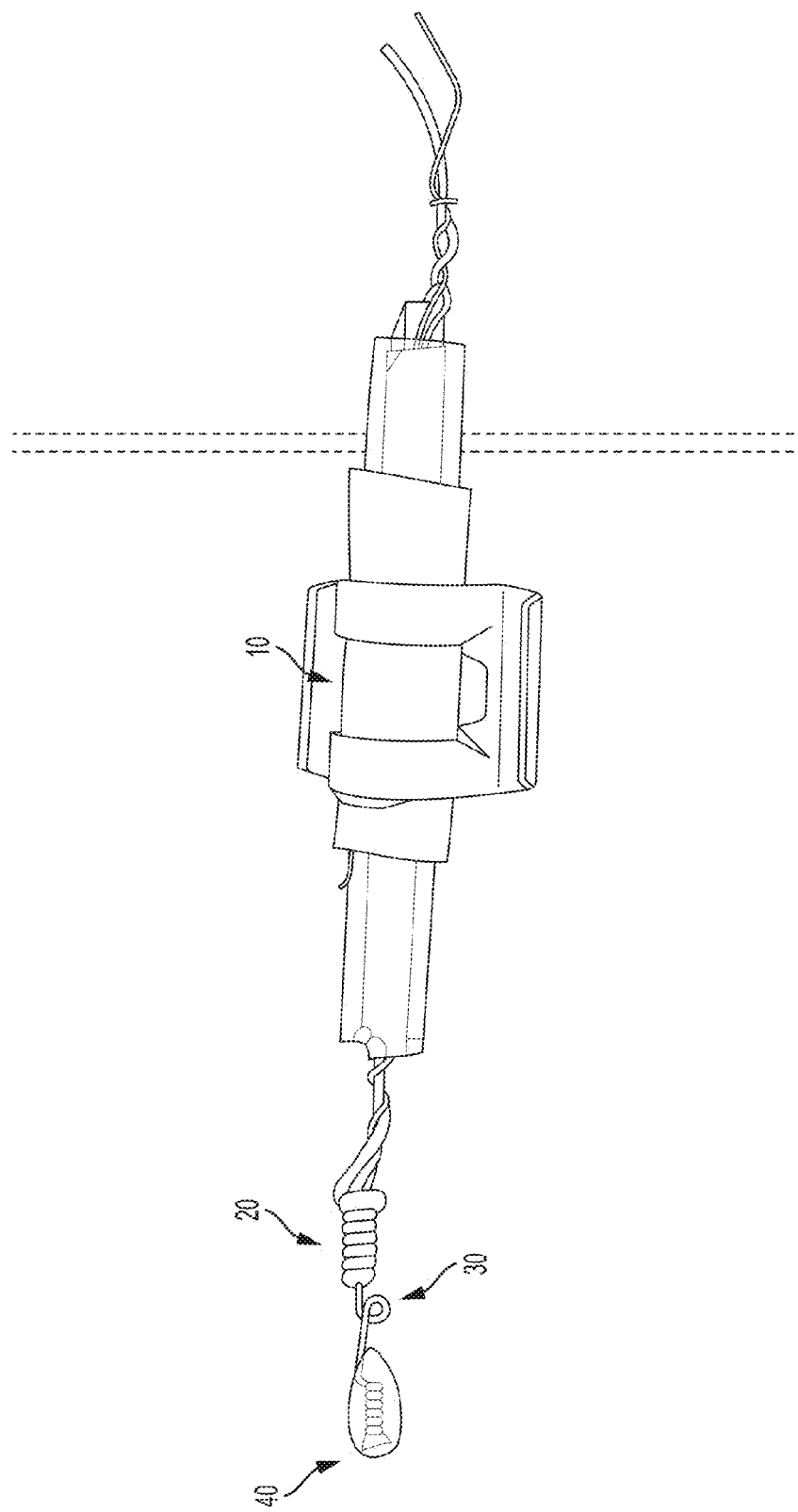
FIG. 13 shows an implantable glucose sensor. The double dotted line represents the skin and all components of glucose sensor shown to the left of the double dotted line are implanted in the skin; all components of the glucose sensor shown to the right of the double dotted line are outside the skin.
Figure 14:
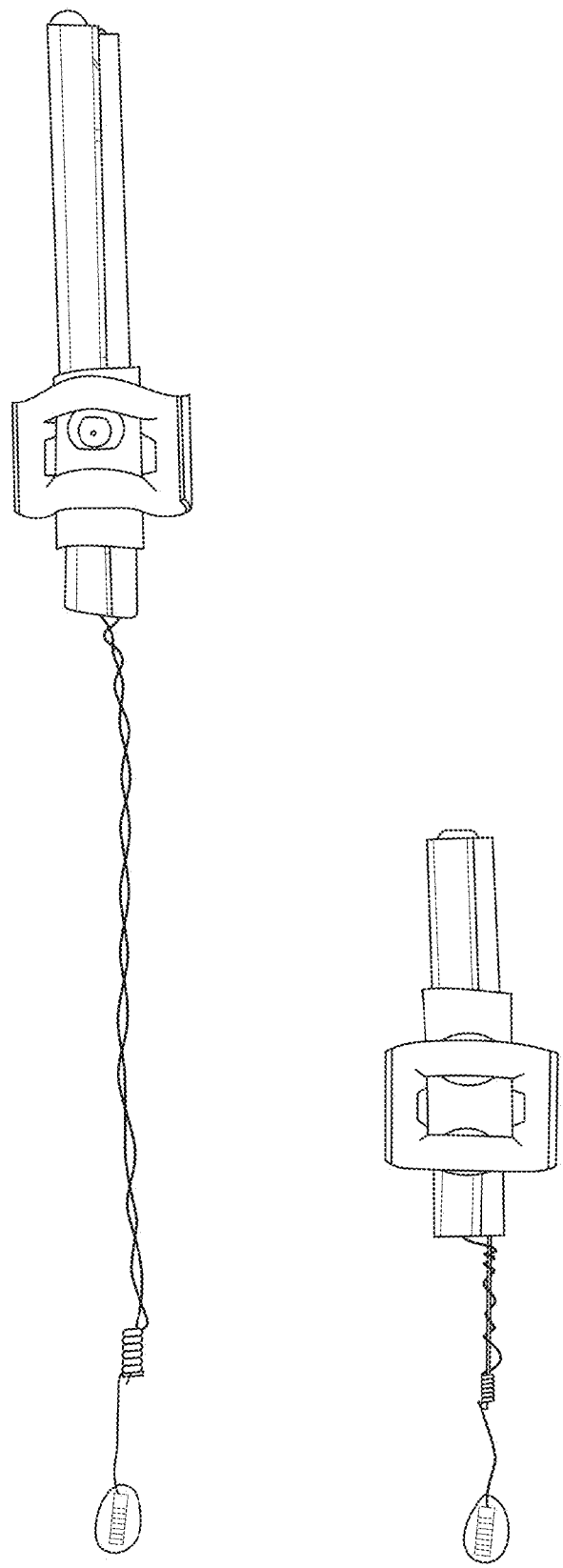
FIG. 14 shows implantable glucose sensors. The glucose sensor in the upper portion of the figure has a long wire (30 mm). The glucose sensor in the lower portion of the figure has a short wire (10 mm).
Figure 15A:
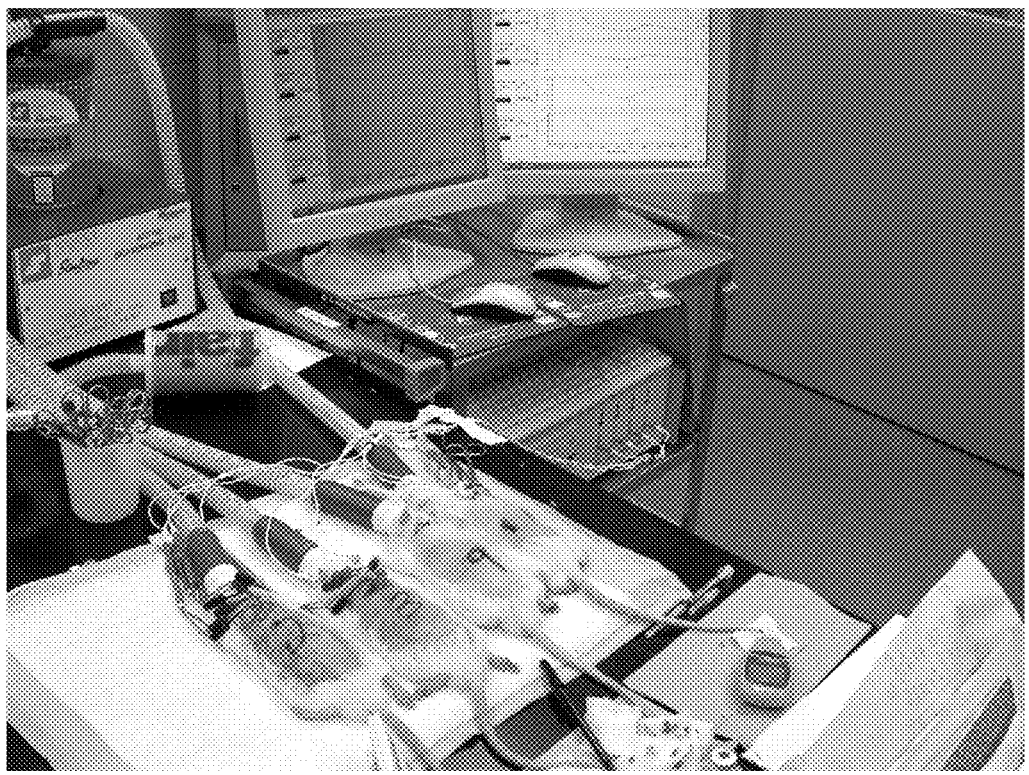
FIGS. 15A-15C show the in vivo study with the glucose sensors implanted in the backs of rats.
Figure 15B:
Figure 15C:

An implantable glucose sensor used in these studies is shown in FIG. 13 having a multi-layered sensing element as shown in FIG. 1. The wound clip is shown as 10, the Ag/AgCl Reference Counter Electrode is shown as 20, the loop is shown as 30, and the sensor with scaffold Pt/Ir electrode is labeled 40. In the in vitro study, 16 sensors were placed in PBS (pH 7.4) at 37° C. for four weeks. Sensitivity was measured at given time intervals (weeks 1 to 4) using potentiostat (WPI, Inc.). Sensitivity (nA/mM)= ($I_{15\ mM}$-$I_{5\ mM}$)/(15 mM-5 mM). In the in vivo study, 48 sensors (24-short wire) were implanted subcutaneously in the backs of rats and sensitivities measured weekly under anesthesia using a 4-channel potentiostat (WPI, Inc.) (see FIGS. 14 and 15). Sensitivity (nA/mM)=$(I_{max}-I_0)/(C_{max}-C_0)$. Concentration of blood glucose (C) was measured using a standard FREESTYLE Glucometer.

Figure 17:
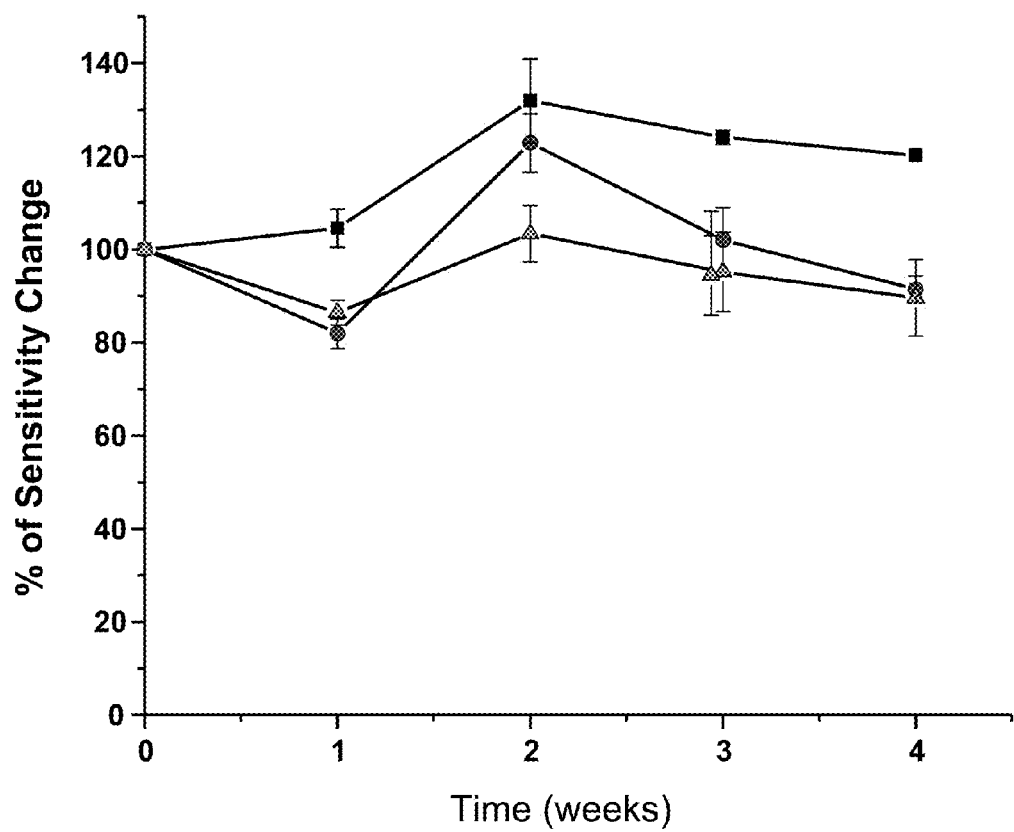
FIG. 17 is a graph of change in sensitivity (%) of the sensor versus time; the control (no scaffold) is shown by filled-in squares; the sensor with NDGA cross-linked scaffold is shown by filled in circles; the sensor with GA cross-linked scaffold is shown by filled-in triangles.

As shown in FIG. 16, hydrated NDGA-reinforced collagen scaffolds had higher form stability than GA cross-linked collagen scaffolds. In regard to in vitro sensitivity, a slight decrease of the sensitivity was observed in the presence of the scaffold. However, both sensors with scaffold retained above 80% of their original sensitivity up to four weeks in vitro (see FIG. 17). Thus, three dimensional scaffold application around glucose sensors did not seriously affect sensor sensitivity in vitro.

Figure 18:
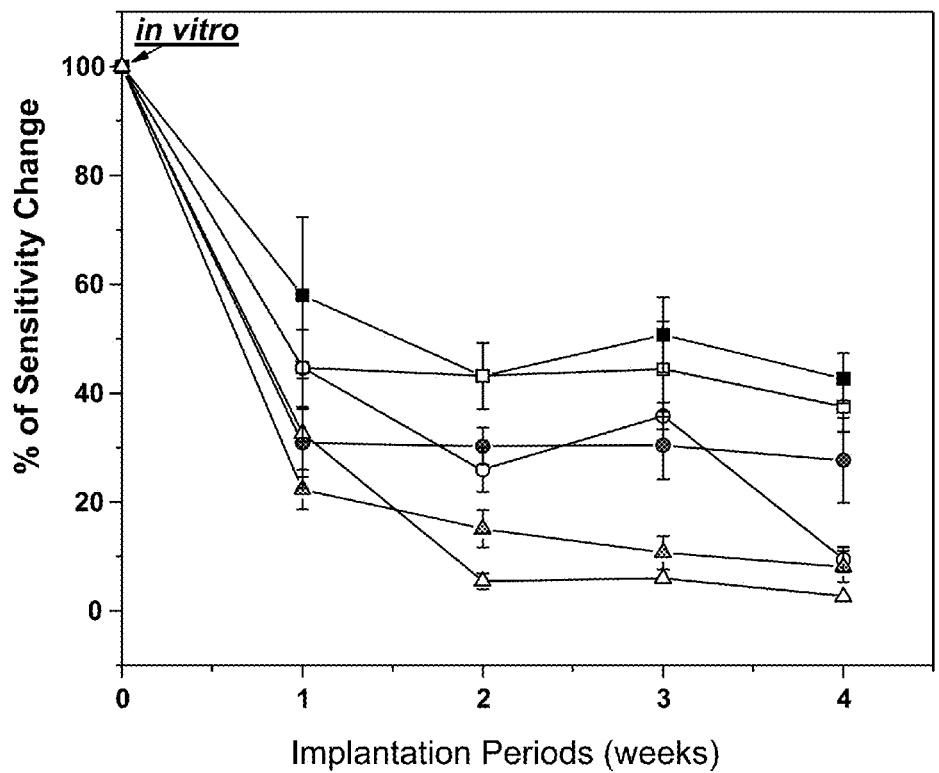
FIG. 18 is a graph of change in sensitivity (%) of sensor versus implantation periods (weeks). The control (no scaffold) with a short-wire sensor is shown by filled-in squares (6 working sensors out of 8 implanted sensors); the control (no scaffold) with a long-wire sensor is shown by open squares (4 working sensors out of 8 implanted sensors); the short-wire sensor with NDGA cross-linked scaffold is shown by filled-in circles (4 working sensors out of 8 implanted sensors); the long-wire sensor with is NDGA cross-linked scaffold is shown by open circles (2 working sensors out of 8 implanted sensors); the short-wire sensor with GA cross-linked scaffold is shown by filled-in triangles (4 working sensors out of 8 implanted sensors); the long-wire sensor with GA cross-linked scaffold is shown by open triangles (1 working sensor out of 8 implanted sensors).

In regard to in vivo sensitivity of the implanted glucose sensor, short-wired sensors showed better performance overall than long-wired sensors due to limitation of micromotion in short-wired sensors. Sensors with NDGA-reinforced scaffolds retained much higher sensitivity after four weeks implantation than sensors with GA cross-linked scaffolds (see FIG. 18).

Figure 19A:
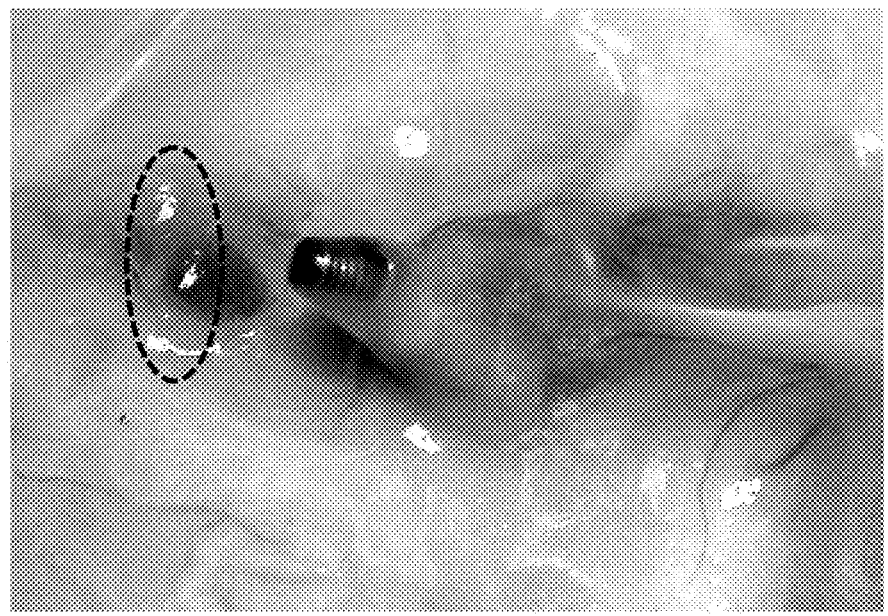
FIG. 19A-19C are photographs of the implanted glucose sensor showing physical stability of the collagen scaffold after four weeks of implantation.
Figure 19B:
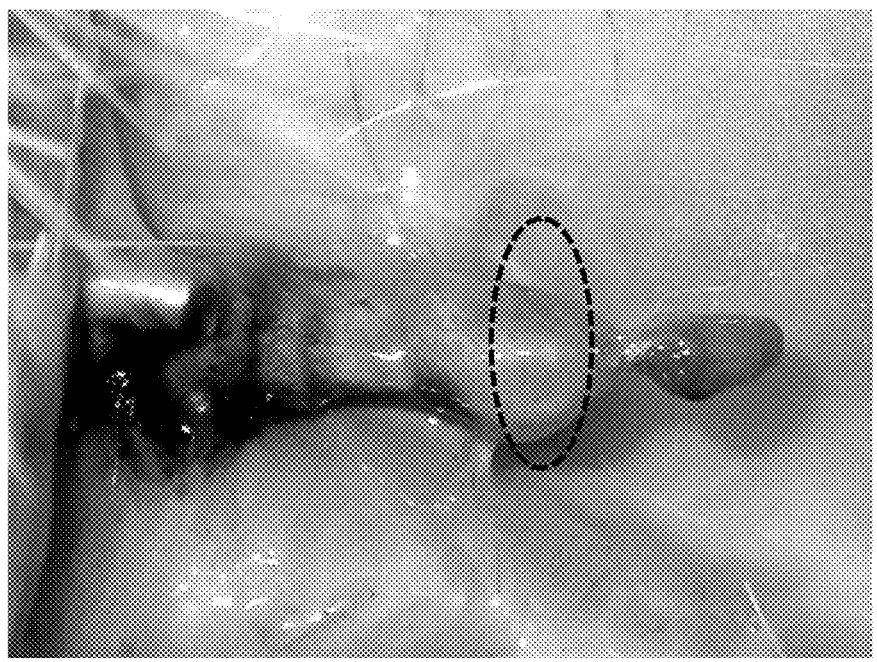
Figure 19C:
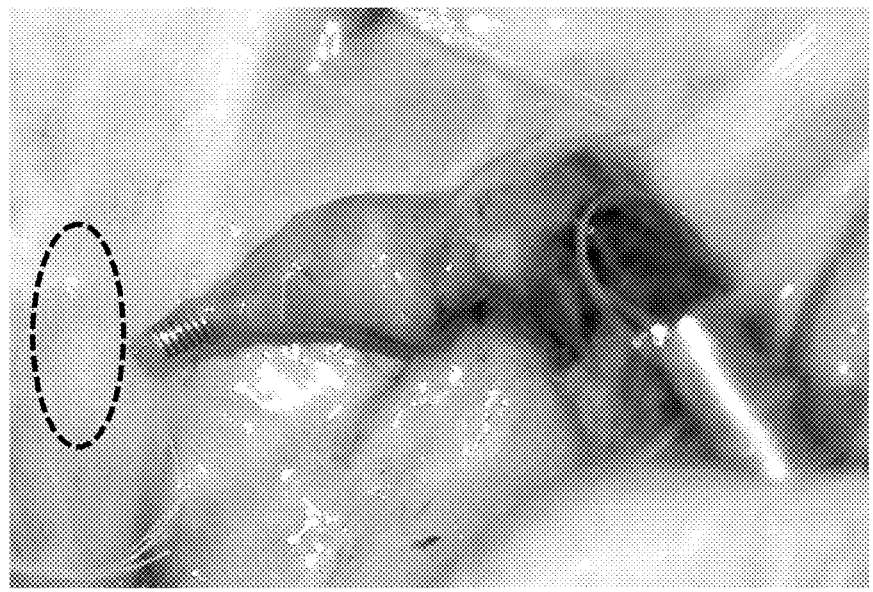
Figure 20A:
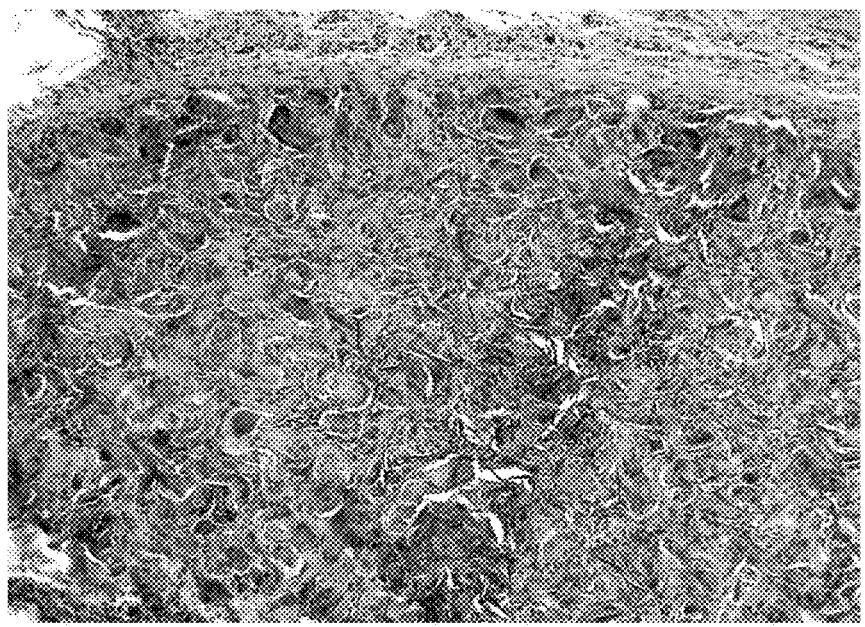
FIGS. 20A-20B are digital images of tissue subjected to histological assay (scaffold without sensors).
Figure 20B:
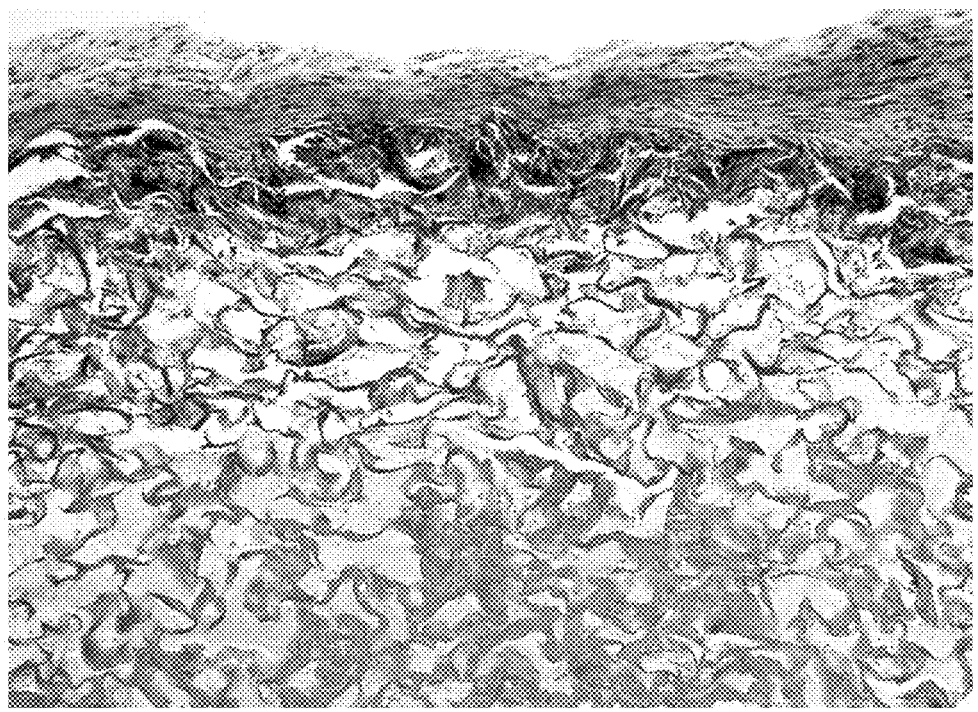

In regard to physical stability and sensitivity of the implanted glucose sensor, short-wired sensors with NDGA-reinforced collagen scaffolds had much higher sensitivity and physical stability than sensors with AG cross-linked scaffolds during four weeks in vivo (see FIGS. 19 and 20).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,821,530
U.S. Pat. No. 6,565,960
Angele P, Abke J, Kujat R, Faltermeier H, Schumann D, Nerlich M, Kinner B, Englert C, Ruszczak Z, Mehrl R and others. Influence of different collagen species on physicochemical properties of crosslinked collagen matrices. Biomaterials 2004; 25 (14):2831-41.
Armour J C, Lucisano J Y, McKean B D, Gough D A. Application of chronic intravascular blood glucose sensor in dogs. Diabetes 1990; 39 (12):1519-26.
Ash S R, Poulos J T, Rainier J B, Zopp W E, Janle E, Kissinger P T. Subcutaneous capillary filtrate collector for measurement of blood glucose. Asaio J 1992; 38 (3): M416-20.
Barbani N, Giusti P, Lazzeri L, Polacco G, Pizzirani G. Bioartificial materials based on collagen: 1. Collagen cross-linking with gaseous glutaraldehyde. J Biomater Sci Polym Ed 1995; 7 (6):461-9.
Bindra D S, Zhang Y, Wilson G S, Sternberg R, Thevenot D R, Moatti D, Reach G. Design and in vitro studies of a needle-type glucose sensor for subcutaneous monitoring. Anal Chem 1991; 63 (17):1692-6.
Chvapil M, Kronenthal L, Van Winkle W, Jr. Medical and surgical applications of collagen. Int Rev Connect Tissue Res 1973; 6:1-61.
Ertefai S, Gough D A. Physiological preparation for studying the response of subcutaneously implanted glucose and oxygen sensors. J Biomed Eng 1989; 11 (5):362-8.
Frost M C, Meyerhoff M E. Implantable chemical sensors for real-time clinical monitoring: progress and challenges. Curr Opin Chem Biol 2002; 6 (5):633-41.
Huang-Lee L L, Cheung D T, Nimni M E. Biochemical changes and cytotoxicity associated with the degradation of polymeric glutaraldehyde derived crosslinks. J Biomed Mater Res 1990; 24 (9):1185-201.
Johnson K W, Mastrototaro J J, Howey D C, Brunelle R L, Burden-Brady P L, Bryan N A, Andrew C C, Rowe H M, Allen D J, Noffke B W and others. In vivo evaluation of an electroenzymatic glucose sensor implanted in subcutaneous tissue. Biosens Bioelectron 1992; 7 (10):709-14.
Joseph J I, Torjman M J. Glucose Sensors. In: Wnek G E, Bowlin G L, editors. Encyclopedia of biomaterials and biomedical engineering. New York: Marcel Dekker; 2004. p 683-692.
Kerner W, Kiwit M, Linke B, Keck F S, Zier H, Pfeiffer E F. The function of a hydrogen peroxide-detecting electroenzymatic glucose electrode is markedly impaired in human sub-cutaneous tissue and plasma. Biosens Bioelectron 1993; 8 (9-10):473-82.
Khor E. Methods for the treatment of collagenous tissues for bioprostheses. Biomaterials 1997; 18 (2):95-105.
Koob T J, Hernandez D J. Material properties of polymerized NDGA-collagen composite fibers: development of biologically based tendon constructs. Biomaterials 2002b; 23 (1):203-12.
Koob T J, Willis T A, Hernandez D J. Biocompatibility of NDGA-polymerized collagen fibers. I. Evaluation of cytotoxicity with tendon fibroblasts in vitro. J Biomed Mater Res 2001a; 56 (1):31-9.
Koob T J, Willis T A, Qiu Y S, Hernandez D J. Biocompatibility of NDGA-polymerized collagen fibers. II. Attachment, proliferation, and migration of tendon fibroblasts in vitro. J Biomed Mater Res 2001b; 56 (1):40-8.
Koob T J. Biomimetic approaches to tendon repair. Comp Biochem Physiol A Mol Integr Physiol 2002a; 133 (4): 1171-92.
Koob T J. Collagen Fixation. In: Wnek G E, Bowlin G L, editors. Encyclopedia of biomaterials and biomedical engineering. New York: Marcel Dekker; 2004. p 335-347.
Koudelka M, Rohner-Jeanrenaud F, Terrettaz J, Bobbioni-Harsch E, de Rooij N F, Jeanrenaud B. In-vivo behaviour of hypodermically implanted microfabricated glucose sensors. Biosens Bioelectron 1991; 6 (1):31-6.
Lee C H, Singla A, Lee Y. Biomedical applications of collagen. Int J Pharm 2001; 221 (1-2):1-22.
Lee S, Nayak V, Dodds J, Pishko M, Smith N B. Glucose measurements with sensors and ultrasound. Ultrasound Med Biol 2005; 31 (7):971-7.
Long N, Yu B, Moussy Y, Moussy F. Strategies for testing long-term transcutaneous amperometric glucose sensors. Diabetes Technol Ther 2005; 7 (6):927-36.
Meyerhoff C, Bischof F, Sternberg F, Zier H, Pfeiffer E F. On line continuous monitoring of subcutaneous tissue glucose in men by combining portable glucosensor with microdialysis. Diabetologia 1992; 35 (11):1087-92.
Moscone D, Mascini M. Microdialysis and glucose biosensor for in vivo monitoring. Ann Biol Clin (Paris) 1992; 50 (5):323-7.
Moussy F, Harrison D J, O'Brien D W, Rajotte R V. Performance of subcutaneously implanted needle-type glucose sensors employing a novel trilayer coating. Anal Chem 1993; 65 (15):2072-7.

Moussy F, Harrison D J, Rajotte R V. A miniaturized Nafion-based glucose sensor: in vitro and in vivo evaluation in dogs. Int J Artif Organs 1994b; 17 (2):88-94.

Moussy F, Harrison D J. Prevention of the rapid degradation of subcutaneously implanted Ag/AgCl reference electrodes using polymer coatings. Anal Chem 1994c; 66 (5):674-9.

Moussy F, Jakeway S, Harrison D J, Rajotte R V. In vitro and in vivo performance and lifetime of perfluorinated ionomer-coated glucose sensors after high-temperature curing. Anal Chem 1994a; 66 (22):3882-8.

Pachence J M. Collagen-based devices for soft tissue repair. J Biomed Mater Res 1996; 33 (1):35-40.

Patel V R, Amiji M M. Preparation and characterization of freeze-dried chitosan-poly(ethylene oxide) hydrogels for site-specific antibiotic delivery in the stomach. Pharm Res 1996; 13 (4):588-93.

Pickup J C, Shaw G W, Claremont D J. In vivo molecular sensing in diabetes mellitus: an implantable glucose sensor with direct electron transfer. Diabetologia 1989; 32 (3):213-7.

Pieper J S, van der Kraan P M, Hafmans T, Kamp J, Buma P, van Susante J L, van den Berg W B, Veerkamp J H, van Kuppevelt T H. Crosslinked type II collagen matrices: preparation, characterization, and potential for cartilage engineering. Biomaterials 2002; 23 (15):3183-92.

Quinn C P, Pathak C P, Heller A, Hubbell J A. Photo-crosslinked copolymers of 2-hydroxyethyl methacrylate, poly(ethylene glycol) tetra-acrylate and ethylene dimethacrylate for improving biocompatibility of biosensors. Biomaterials 1995; 16 (5):389-96.

Reddy S M, Vadgama P M. Ion exchanger modified PVC membranes—selectivity studies and response amplification of oxalate and lactate enzyme electrodes. Biosens Bioelectron 1997; 12 (9-10):1003-12.

Reichert W M, Saavedra S S. Materials considerations in the selection, performance, and adhesion of polymeric encapsulants for implantable sensors. In: Williams D F, editor. Medical and Dental Materials. New York: VCH Publishers, Inc.; 1992. p 303-343.

Reichert W M, Sharkawy A A. Chap. 28 Biosonsors In: Von Recum A, editor. Handbook of biomaterials evaluation : scientific, technical, and clinical testing of implant materials. Philadelphia: Taylor & Francis; 1999. p 439-460.

Rigby G P, Crump P, Vadgama P. Open flow microperfusion: approach to in vivo glucose monitoring. Med Biol Eng Comput 1995; 33 (2):231-4.

Sharkawy A A, Klitzman B, Truskey G A, Reichert W M. Engineering the tissue which encapsulates subcutaneous implants. I. Diffusion properties. J Biomed Mater Res 1997; 37 (3):401-12.

Sharkawy A A, Neuman M R, Reichert W M. Sensocompatibility: Design considerations for biosensor-based drug delivery systems. In: Park K, editor. Controlled Drug Delivery: The Next Generation. Washington, DC: American Chemical Society, 2007.

Shaw G W, Claremont D J, Pickup J C. In vitro testing of a simply constructed, highly stable glucose sensor suitable for implantation in diabetic patients. Biosens Bioelectron 1991; 6 (5):401-6.

Sheu M T, Huang J C, Yeh G C, Ho H O. Characterization of collagen gel solutions and collagen matrices for cell culture. Biomaterials 2001; 22 (13):1713-9.

Shichiri M, Asakawa N, Yamasaki Y, Kawamori R, Abe H. Telemetry glucose monitoring device with needle-type glucose sensor: a useful tool for blood glucose monitoring in diabetic individuals. Diabetes Care. Volume 9; 1986. p 298-301.

Shichiri M, Yamasaki Y, Nao K, Sekiya M, Ueda N. In vivo characteristics of needle-type glucose sensor—measurements of subcutaneous glucose concentrations in human volunteers. Horm Metab Res Suppl 1988; 20:17-20.

Sung H W, Hsu H L, Shih C C, Lin D S. Cross-linking characteristics of biological tissues fixed with monofunctional or multifunctional epoxy compounds. Biomaterials 1996; 17 (14):1405-10.

van Luyn M J, van Wachem P B, Olde Daminik L H, Dijkstra P J, Feijen J, Nieuwenhuis P. Secondary cytotoxicity of cross-linked dermal sheep collagens during repeated exposure to human fibroblasts. Biomaterials 1992; 13 (14):1017-24.

Wilkins E, Atanasov P, Muggenburg B A. Integrated implantable device for long-term glucose monitoring. Biosens Bioelectron 1995; 10 (5):485-94.

Yu B, Long N, Moussy Y, Moussy F. A long-term flexible minimally-invasive implantable glucose biosensor based on an epoxy-enhanced polyurethane membrane. Biosens Bioelectron 2006; 21 (12):2275-82.

We claim:

1. A device having enhanced biocompatibility for implantation into the body or tissue of a person or animal, wherein said device comprises a biocompatible collagen scaffold and/or coating embedded in a nordihydroguaiaretic acid (NDGA) bisquinone polymer matrix; and wherein said device comprises a sensor.

2. The device according to claim 1, wherein said device is a glucose sensor.

3. The device according to claim 1, wherein said device comprises an epoxy coating underneath said collagen scaffold and/or coating.

4. The device according to claim 3, wherein said epoxy coating is an epoxy-polyurethane coating.

5. The device according to claim 1, wherein said collagen scaffold and/or coating comprises open pores of about 10 μm to about 200 μm in diameter (mean).

6. The device according to claim 5, wherein the mean pore size of said collagen scaffold and/or coating is about 60 μm or less in diameter.

7. The device according to claim 5, wherein the mean pore size of said collagen scaffold and/or coating is between about 40 μm to about 80 μm in diameter.

8. The device according to claim 5, wherein said pores are regularly distributed in said collagen scaffold and/or coating.

9. The device according to claim 5, wherein said pores form an interconnected pore structure in said collagen scaffold and/or coating.

10. The device according to claim 1, wherein said collagen scaffold and/or coating comprises an antimicrobial, anti-inflammatory, and/or angiogenic compound, drug or growth factor.

* * * * *